(12) United States Patent
Ueno et al.

(10) Patent No.: US 6,252,104 B1
(45) Date of Patent: Jun. 26, 2001

(54) NAPHTHOL DERIVATIVES AND PROCESS FOR PRODUCING THE SAME

(75) Inventors: Ryuzo Ueno; Shigeru Ito, both of Hyogo; Kenji Minami, Osaka; Masaya Kitayama, Hyogo, all of (JP)

(73) Assignee: Kabushiki Kaisha Ueno Seiyaku Oyo Kenkyujo, Osaka (JP)

( * ) Notice: Subject to any disclaimer, the term of this patent is extended or adjusted under 35 U.S.C. 154(b) by 0 days.

(21) Appl. No.: 08/764,269

(22) PCT Filed: Apr. 10, 1996

(86) PCT No.: PCT/JP96/00979

§ 371 Date: Dec. 12, 1996

§ 102(e) Date: Dec. 12, 1996

(87) PCT Pub. No.: WO96/32366

PCT Pub. Date: Oct. 17, 1996

(30) Foreign Application Priority Data

Apr. 12, 1995 (JP) .................................................. 7-086784

(51) Int. Cl.[7] .................................................. C07C 229/00

(52) U.S. Cl. .......................... 560/42; 548/306.4; 548/444; 552/236; 552/256; 560/34; 560/139; 560/56; 562/439; 562/451; 562/840; 564/44; 564/156

(58) Field of Search ........................................ 568/735, 737, 568/929, 665; 560/100, 42, 34, 139; 564/152, 157, 158, 44, 156; 552/236, 256; 562/439, 451, 840; 548/306.4, 444

(56) References Cited

FOREIGN PATENT DOCUMENTS

4316937 * 5/1993 (DE) .
6340582 12/1994 (JP) .
6340583 12/1994 (JP) .

OTHER PUBLICATIONS

Streitwieser et al., Intro to Organic Chemistry, pp 460–461, 1973.*

Silverman, R. B., The Organic Chemistry of Drug Design and Drug Action. (No Year).*

* cited by examiner

Primary Examiner—Michael L. Shippen
(74) Attorney, Agent, or Firm—Sughrue, Mion, Zinn, Macpeak & Seas, PLLC

(57) ABSTRACT

A naphthol derivative represented by the general formula (I), [wherein Y and Y' indicate —(CONH)$_n$—X or —COR; X is a phenyl group, a naphthyl group, an anthraquinonyl group, a benzimidazolonyl group or a carbazolyl group; R is a hydroxyl group, an alkoxy group having 1 to 6 carbon atoms, a halogen atom, a benzyloxy group, a phenyloxy group or a phenacyloxy group; $R_2$ is a hydrogen atom, an alkaline metal, an alkyl group having 1 to 6 carbon atoms, an acyl group having 1 to 6 carbon atoms or a phenylalkyl group; Z is a group selected from the group consisting of a hydrogen atom, a halogen atom, a nitro group, a nitroso group and an amino group (Z may be substituted on any ring of the naphthalene ring); and n is an integer of 1 or 2; provided that $R_2$ and Z do not simultaneously indicate a hydrogen atom when both R simultaneously indicate a hydroxyl group], and a process for producing the same. This naphthol derivative can be used as raw materials for synthesis, such as dyes, pigments, photosensitive materials and the like.

(I)

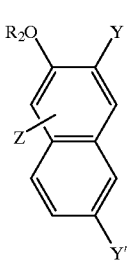

4 Claims, 36 Drawing Sheets

NAPHTHOL DERIVATIVES AND PROCESS FOR PRODUCING THE SAME

TECHNICAL FIELD

The present invention relates to a novel naphthol derivatives which can be used as raw materials etc. for synthesis, such as dyes, pigments, photosensitive materials and the like, and a process for producing the same.

BACKGROUND ART

The naphthol derivatives is the cheapest among condensed aromatic compounds which form a conjugated polyene system and has absorption in the electron band, and is easily used as raw materials for synthesis. Therefore, it has hitherto been used as various peculiar compounds, particularly raw materials such as dyes, pigments, photosensitive materials and the like.

As the naphthol derivatives like this, for example, there have been known 2-hydroxy-3-phenylaminocarbonylnaphthalene or 2-hydroxy-6-phenylaminocarbonylnaphthalene wherein a substituent is introduced at the 3-position or 6-position of 2-hydroxynaphthalene, and those wherein an alkyl or alkoxy group is added to these phenyl groups.

But as the naphthalene derivative which has substituents at both the 3-position and 6-position of 2-hydroxynaphthalene, 2-hydroxy-3,6-dihydroxycarbonylnaphthalene is merely known.

An object of the present invention is to provide novel derivatives of 3,6-di-substituted-2-hydroxynaphthalene, particularly 2-hydroxy-3,6-dihydroxycarbonylnaphthalene, which is useful as raw materials for synthesis, and a process for synthesizing the same.

DISCLOSURE OF THE INVENTION

The present invention relates to naphthol derivatives represented by the general formula (I):

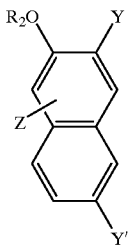

(I)

[wherein
Y is —(CONH)$_n$—X or —COR;
Y' is —(CONH)$_n$—X' or —COR';
X and X' may be the same or different and indicate a phenyl group, a naphthyl group, an anthraquinonyl group, a benzimidazolonyl group or a carbazolyl group, and each group may be optionally substituted;
R and R' may be the same or different and indicate a hydroxyl group, an optically branched alkoxy group having 1 to 6 carbon atoms, a halogen atom, a benzyloxy group, a phenyloxy group or a phenacyloxy group;
R$_2$ is a hydrogen atom, an alkaline metal, an optionally branched alkyl group having 1 to 6 carbon atoms, an acyl group having 1 to 6 carbon atoms or a phenylalkylene group;

Z indicated one or more sorts of groups selected from the group consisting of a hydrogen atom, a halogen atom, a nitro group, a nitrosos group and an amino group (Z may be substituted on any ring of the naphthalene ring); and
n is an integer of 1 or 2;
provided that R$_2$ and Z are not simultaneously hydrogen atom when R and R' simultaneously are hydroxyl group], and a process for producing the same.

Particularly, the present invention relates to naphthol derivatives represented by the general formula (IV)

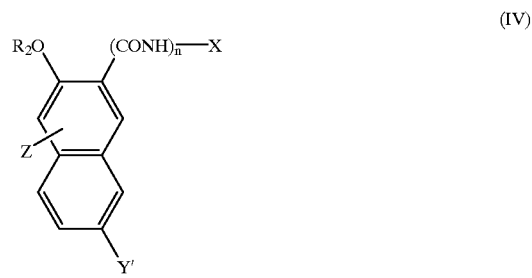

(IV)

or (IV'):

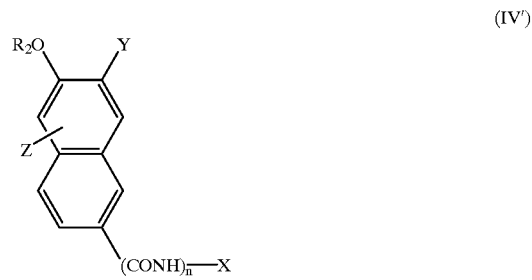

(IV')

wherein one of Y and Y' is —(CONH)$_n$—X and the other is —(CONH)$_n$—X or COR in the general formula (I) [X, n and R are as defined above].

More particularly, the present invention relates to naphthol derivatives represented by the general formula (V):

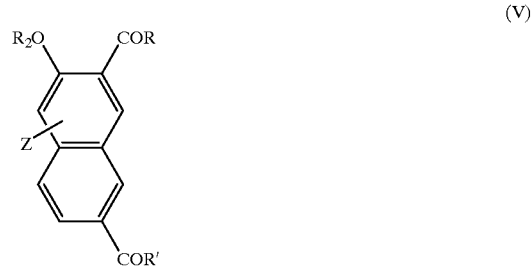

(V)

wherein Y and Y' are respectively represented by COR and COR' in the general formula (I) [R and R' are as defined above, provided that R$_2$ and Z are not simultaneously hydrogen atom when R and R' simultaneously are hydroxyl group].

The naphthol derivative (I) of the present invention is a novel naphthol derivative compound.

The naphthol derivatives (IV) and (IV') of the present invention are novel compounds, and are compounds wherein an optionally substituted phenyl, naphthyl, anthraquinonyl, benzimidazolonyl or carbazolyl group is added at the 3-position and/or 6-position of 2-hydroxynaphthalene through an aminocarbonyl or —CONHCONH group. These residues, which are added through the aminocarbonyl or —CONHCONH group, may be the same or different at the 3-position and 6-position. The aminocarbonyl or —CONHCONH group as a coupling group may also be the same or different at the 3-position and 6-position. Regarding the naphthol derivative of the present invention, one of the 3-position and 6-position may be a hydroxycarbonyl group, an optionally branched alkoxycarbonyl group having 1 to 6 carbon atoms, a benzyloxycarbonyl group, a phenyloxycarbonyl group or a phenacyloxycarbonyl group. The hydrogen atom of the hydroxyl group at the 2-position may be substituted with an alkaline metal atom, an optionally branched alkyl group having 1 to 6 carbon atoms, an acyl group having 1 to 6 carbon atoms or a phenyl-substituted alkylene group. One or more sorts selected from the group consisting of a halogen atom, a nitro group, a nitroso group and an amino group may be introduced into the naphthalene ring.

When X is a substituted form of the phenyl, naphthyl, anthraquinonyl, benzimidazolonyl or carbazolyl group, examples of the substituent include alkyl group, alkoxy group, alkyl halide group, phenoxy group, alkoxycarbonyl group, nitro group, halogen atom, hydroxyl group, amino group, benzoylamino group, dialkylaminosulfonyl group or cyano group. As the alkyl group, an optionally branched saturated or unsaturated alkyl group having 1 to 6 carbon atoms can be used. Preferred examples thereof include methyl, ethyl, propyl, isopropyl, butyl and t-butyl. As the alkoxy group, an optionally branched saturated or unsaturated alkoxy group having 1 to 6 carbon atoms can be used. Preferred examples thereof include methoxy or ethoxy group. Examples of the halogen atom include fluorine, chlorine, bromine and iodine. The number of the substituent is from 1 to 5, and the substituent may be the same or different.

The naphthol derivative (V) of the present invention is also a novel compound, and a compound wherein a hydroxyl group, a halogen atom, an optionally branched alkoxy group having 1 to 6 carbon atoms, a benzyloxy group, a phenyloxy group or a phenacyloxy group is added at the 3-position and 6-position of 2-hydroxynaphthalene through a carbonyl group. The substituents at the 3-position and 6-position may be the same or different. The hydrogen atom of the hydroxyl group at the 2-position may be substituted with an alkaline metal atom, an optionally branched alkyl group having 1 to 6 carbon atoms, an acyl group having 1 to 6 carbon atoms or a phenyl-substituted alkylene group. One or more sorts selected from the group consisting of a halogen atom, a nitro group, a nitroso group and an amino group may be introduced into the naphthalene ring.

The above naphthol derivative (IV) or (IV') of the present invention can be produced by condensing a naphthol derivative represented by the general formula (II):

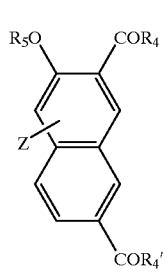
(II)

[wherein $R_4$ is a hydroxyl group or a halogen atom; $R_4'$ is a hydroxyl group, a halogen atom or an optionally branched alkoxy group having 1 to 6 carbon atoms; $R_5$ is a hydrogen atom or a protective group of a hydroxyl group; and Z is as defined above], with an aniline compound represented by the general formula (III):

(III)

[wherein $R_3$ is a single bond or —CONH—; provided that X is as defined above].

$R_5$ in the compound of the formula (II) is a hydrogen atom, an alkaline metal atom or a protective group of a hydroxyl group. The protective group of the hydroxyl group means a group capable of temporarily bonding to a hydroxyl group during the reaction of introducing a substituent into the substitution position which is different from that of the protective group so as to protect the hydroxyl group and then recovering the hydroxyl group easily due to alkaline or acid hydrolysis after the completion of the desirable reaction. Examples thereof include optionally branched alkyl group having 1 to 6 carbon atoms, benzyl group, acetyl group, acetonyl group, tetrahydropyranyl group, trimethylsilyl group and the like.

A phenylurea derivative, wherein $R_3$ in the compound of the formula (III) is —CONH—, can be obtained by forming an ureido group using a cyanate process of reacting the corresponding aniline compound with cyanic acid.

More specifically, as shown in the reaction scheme (VI):

(VI)

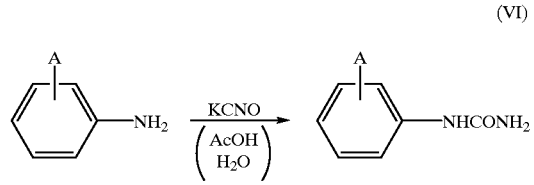

[wherein A is hydrogen or a suitable substituent], the phenylurea derivative can be obtained, for example, by dissolving an aniline compound in an aqueous acetic acid solution, adding dropwise an aqueous potassium cyanate solution at 15° C. over 30 minutes, heating to 30° C. after the completion of the dropwise addition, reacting the mixture for 30 minutes, filtering the deposited crystal, followed by washing with water.

The reaction between the compound (II) and compound (III) can be conducted, for example, by charging 2-hydroxy-3,6-dihydroxycarbonylnaphthalene and an aniline compound in a xylene solvent and adding dropwise $PCl_3$ at 90 to 100° C. Then, the temperature is raised to 140° C. and the reaction is conducted for 3 hours and, after the completion of the reaction, water is added. After neutralizing, the crystal formed by the reaction is filtered and the crystal on a filter paper is washed with an organic solvent (e.g. xylene, etc.) to obtain a compound (IV) or (IV').

In order to introduce a substituent other than the hydrogen atom into $R_2$, for example, a corresponding 3,6-derivative of 2-hydroxy-3,6-dihydroxycarbonylnaphthalene may be reacted with a halide of a residue to be introduced (e.g. benzyl chloride, ethyl iodide, etc.) in the state that the 3-position and 6-position are protected, in the presence of a suitable basic substance (e.g. potassium carbonate, etc.).

In order to introduce halogen at the 1-position, for example, a solution prepared by dissolving a halogen molecule (e.g. bromine, etc.) in chloroform may be added to a solution of a corresponding compound whose 1-position is not substituted. In order to introduce a nitroso group, a solution of the corresponding compound whose 1-position is not substituted may be reacted with an aqueous solution of sodium nitrate.

The naphthol derivative (V) of the present invention can be prepared, for example, by reacting known 2-hydroxy-3,6-dihydroxycarbonyl naphthalene represented by the general formula (VII):

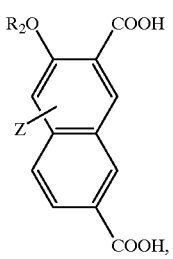

(VII)

or 1-position and/or 2-position substitution products thereof as a starting substance with an organic halide in the presence of a base, or reacting a compound represented by the general formula (VIII):

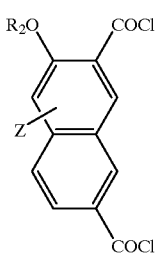

(VIII)

as an acid chloride, which is obtained by chlorinating the compound of the general formula (VII), with alcohols such as lower alcohol having 1 to 6 carbon atoms.

EMBODIMENTS OF THE INVENTION

Figure 1:
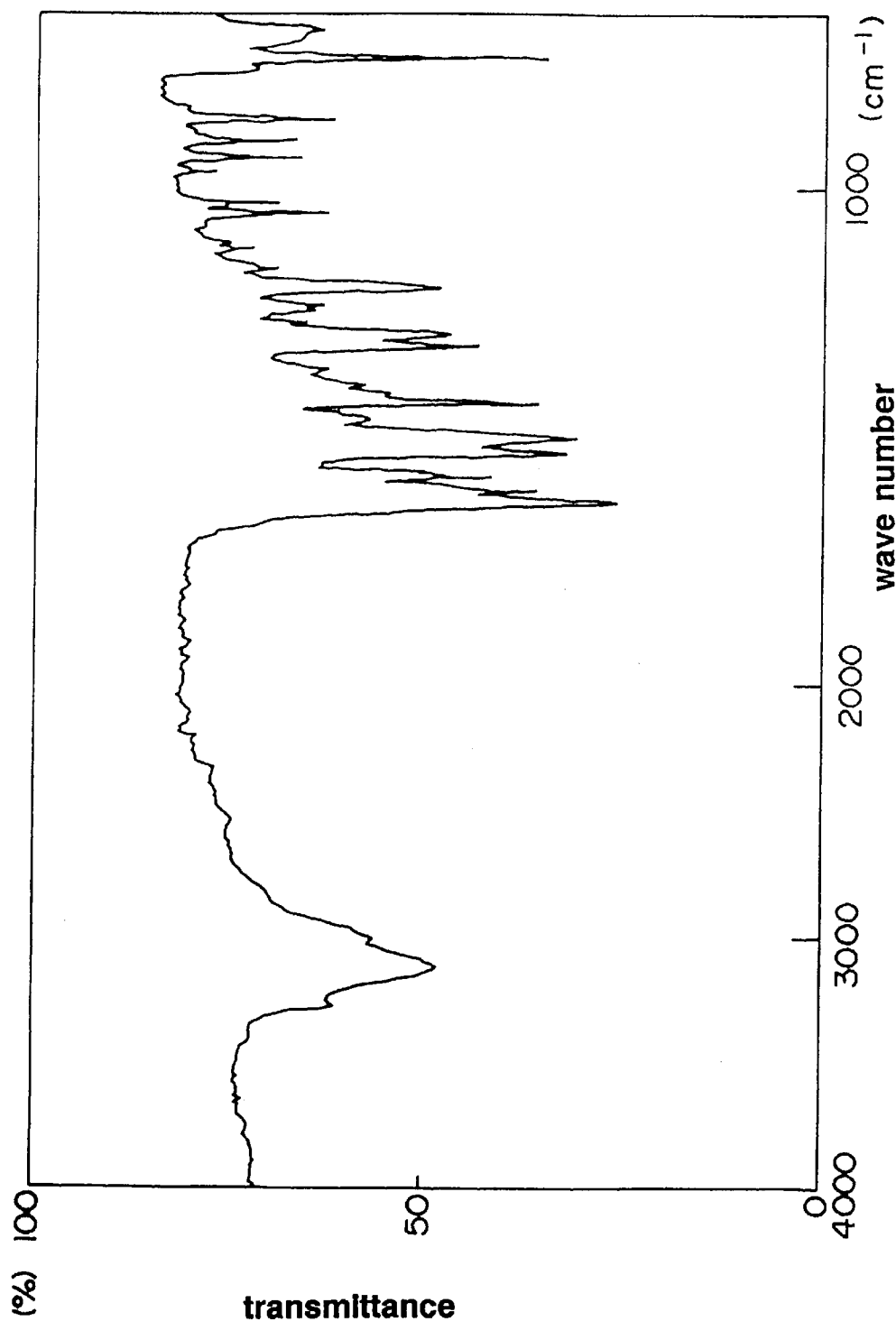
FIG. 1 is a graph illustrating an infrared absorption spectrum of the compound obtained in Example 1.

The following Examples further illustrate the present invention in detail.

EXAMPLE 1

Synthesis of 2-hydroxy-3,6-di-2-chlorophenylaminocarbonylnaphthalene

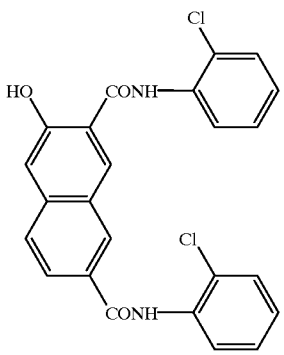

2-Hydroxy-3,6-dihydroxycarbonylnaphthalene (11.6 g) and o-chloroaniline (14.0 g) were dispersed in xylene (232.2 g), followed by heating to 90° C. Phosphorous trichloride (6.0 g) was added dropwise at 90 to 110° C., and then the mixture was reacted at 140° C. for 3 hours. After the completion of the reaction, water (116.1 g) was added and the reaction solution was neutralized with sodium carbonate at 80 to 90° C. The solution was filtered at room temperature and washed in turn with xylene (116.1 g) and water (116.1 g). The resultant crystal was subjected to reflux washing using acetone (80 g) and then filtered. This operation was repeated three times, followed by drying to obtain 14.0 g of 2-hydroxy-3,6-di-2-chlorophenylaminocarbonylnaphthalene as a grayish white powdered crystal (melting point: 267–269° C.).

An infrared spectrum (KBr method) of this compound is shown in FIG. 1.

EXAMPLE 2

Synthesis of 2-hydroxy-3,6-diphenylaminocarbonylnaphthalene

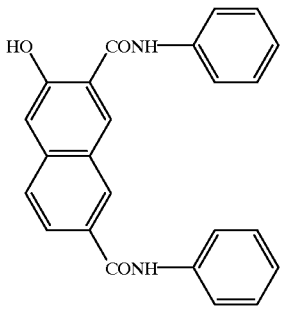

2-Hydroxy-3,6-dihydroxycarbonylnaphthalene (4.64 g) and aniline (4.10 g) were dispersed in xylene (92.8 g), followed by heating to 90° C. Phosphorous trichloride (2.4 g) was added dropwise at 90 to 100° C., and then the mixture was reacted at 140° C. for 3 hours. After the completion of the reaction, water (92.8 g) was added and the reaction solution was neutralized with sodium carbonate at 90° C. The solution was filtered at room temperature and washed in turn with xylene (46.4 g) and water (46.4 g). The resultant crystal was subjected to reflux washing using acetone (80 g) and then filtered. This operation was repeated three times, followed by drying to obtain 3.5 g of 2-hydroxy-3,6-diphenylaminocarbonylnaphthalene as a white powdered crystal (melting point: 314–317° C.).

Figure 2:
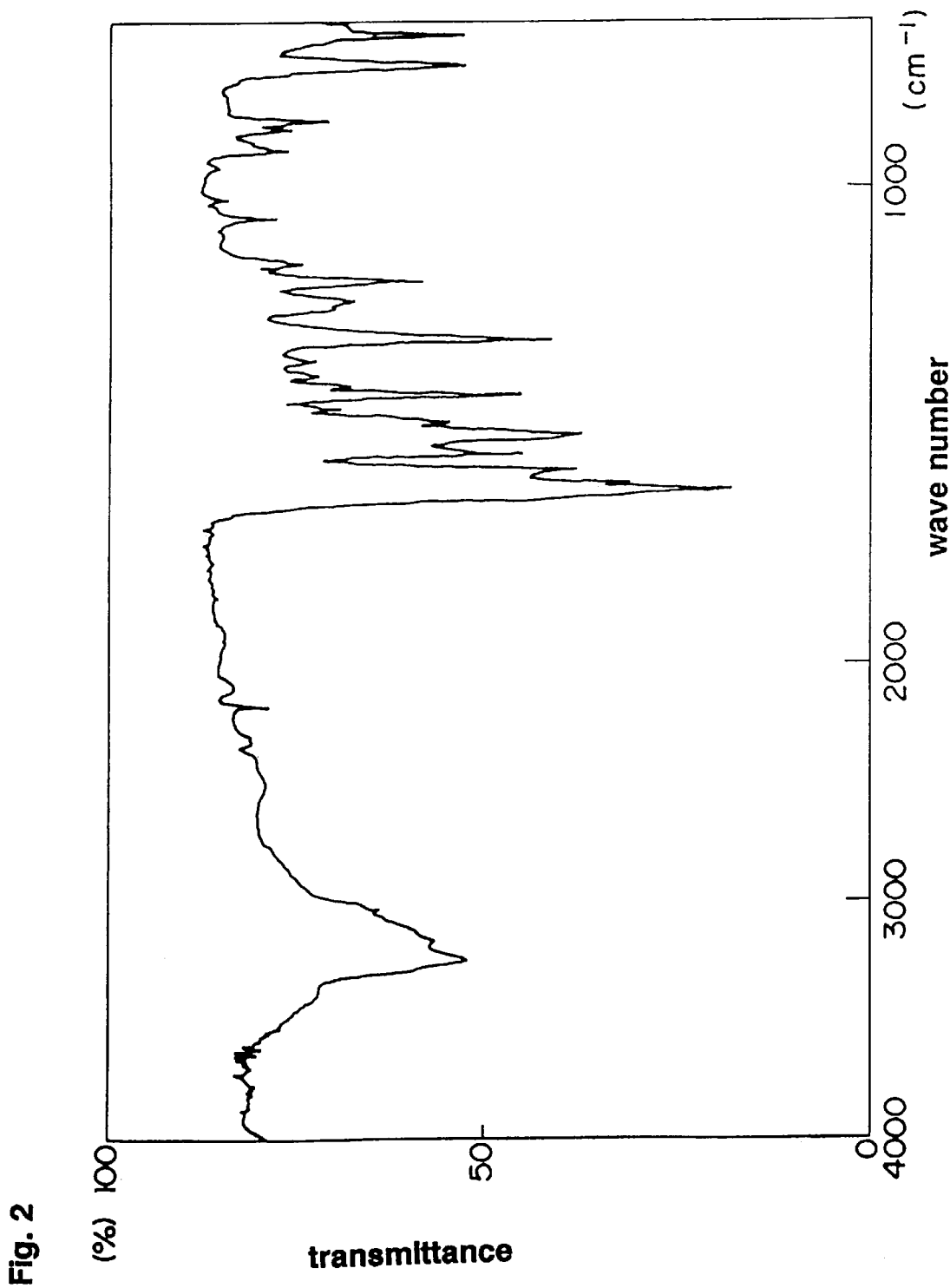
FIG. 2 is a graph illustrating an infrared absorption spectrum of the compound obtained in Example 2.

An infrared spectrum (KBr method) of this compound is shown in FIG. 2.

EXAMPLE 3

Synthesis of 2-hydroxy-3,6-bis(2,4-dimethylphenylaminocarbonyl)naphthalene

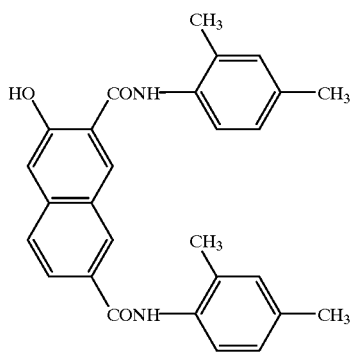

2-Hydroxy-3,6-dihydroxycarbonylnaphthalene (11.6 g) and m-xylidine (13.3 g) were dispersed in xylene (232.2 g), followed by heating to 90° C. Phosphorous trichloride (6.0 g) was added dropwise at 90 to 100° C., and then the mixture was reacted at 140° C. for 3 hours. After the completion of the reaction, water (116.1 g) was added and the reaction solution was neutralized with sodium carbonate at 80 to 90° C. The solution was filtered at room temperature and washed in turn with xylene (116.1 g) and water (116.1 g). The resultant crystal was subjected to reflux washing using acetone (80 g) and then filtered. This operation was repeated three times, followed by drying to obtain 12.9 g of 2-hydroxy-3,6-bis(2,4-dimethylphenylaminocarbonyl)naphthalene as a white powdered crystal (melting point: 284.5–286° C.).

Figure 3:
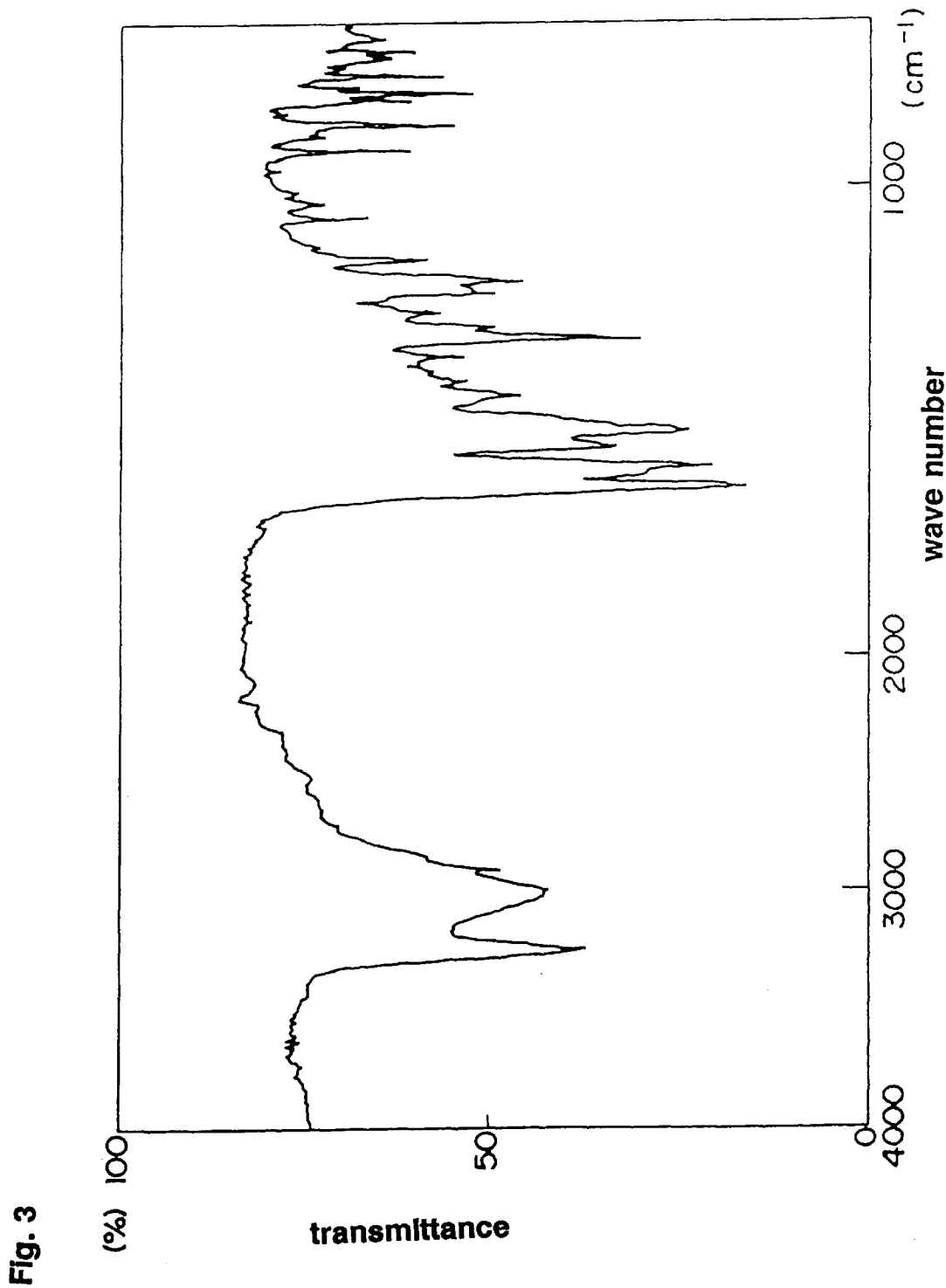
FIG. 3 is a graph illustrating an infrared absorption spectrum of the compound obtained in Example 3.

An infrared spectrum (KBr method) of this compound is shown in FIG. 3.

EXAMPLE 4

Synthesis of 2-hydroxy-3,6-di-2-methylphenylaminocarbonylnaphthalene

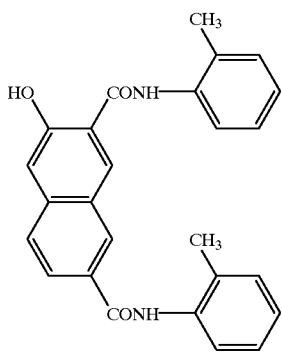

2-Hydroxy-3,6-dihydroxycarbonylnaphthalene (11.6 g) and o-toluidine (12.0 g) were dispersed in xylene (232.2 g), followed by heating to 90° C. Phosphorous trichloride (6.0 g) was added dropwise at 90 to 110° C., and then the mixture was reacted at 140° C. for 3 hours. After the completion of the reaction, water (116.1 g) was added and the reaction solution was neutralized with sodium carbonate at 80 to 90° C. The solution was filtered at room temperature and washed in turn with xylene (116.1 g) and water (116.1 g). The resultant crystal was subjected to reflux washing using acetone (80 g) and then filtered. This operation was repeated three times, followed by drying to obtain 7.8 g of 2-hydroxy-3,6-di-2-methylphenylaminocarbonylnaphthalene as a white powdered crystal (melting point: 264.5–268° C.).

Figure 4:
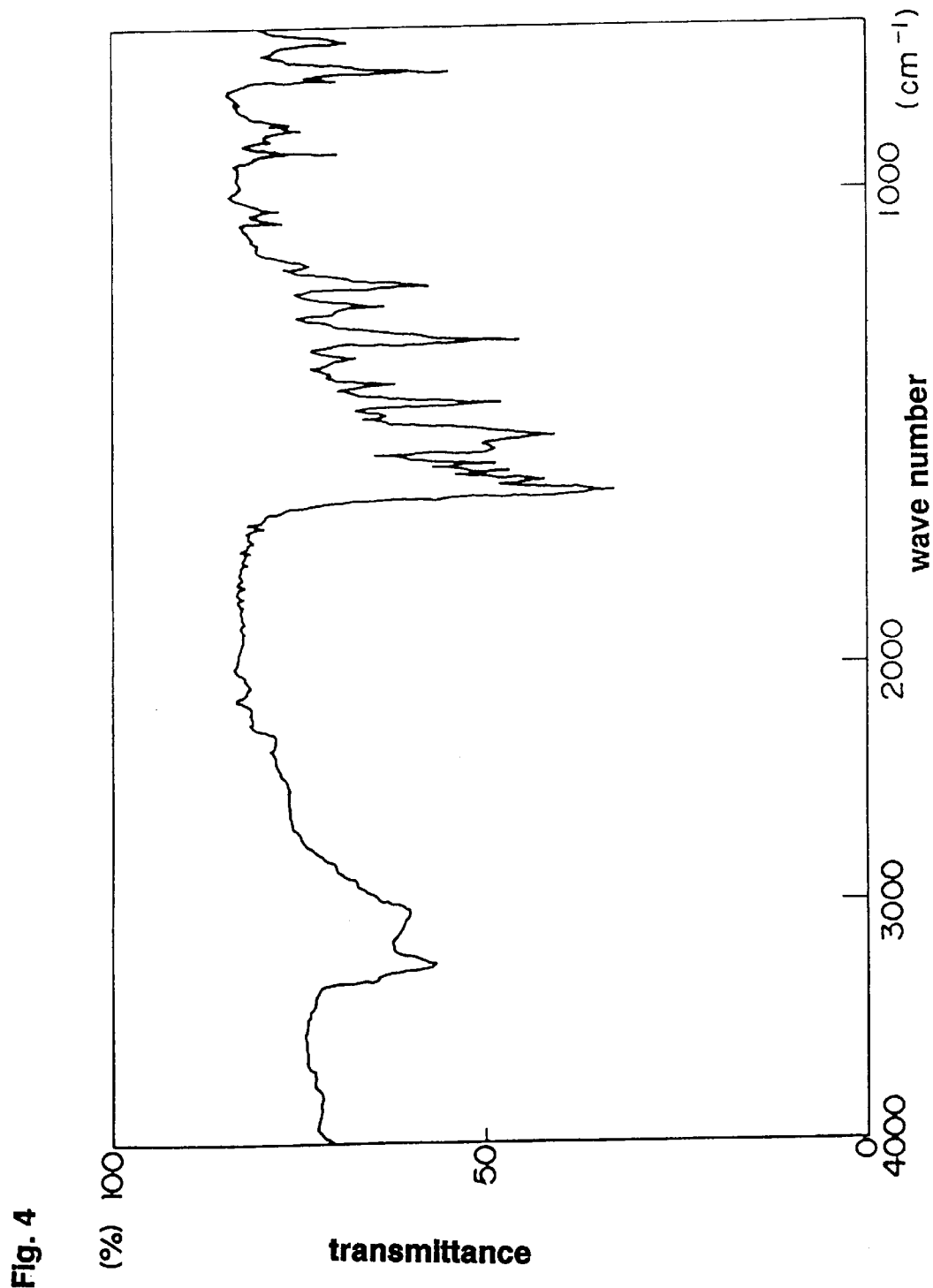
FIG. 4 is a graph illustrating an infrared absorption spectrum of the compound obtained in Example 4.

An infrared spectrum (KBr method) of this compound is shown in FIG. 4.

EXAMPLE 5

Synthesis of 2-hydroxy-3,6-di-2-methoxyphenylaminocarbonylnaphthalene

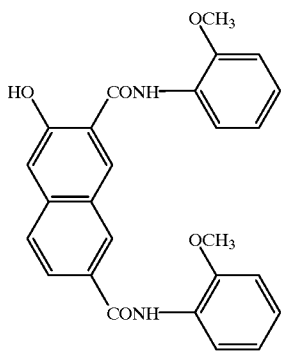

2-Hydroxy-3,6-dicarbonylnaphthalene (11.6 g) and o-anisidine (13.5 g) were dispersed in xylene (232.2 g), followed by heating to 90° C. Phosphorous trichloride (6.0 g) was added dropwise at 90 to 110° C., and then the mixture was reacted at 140° C. for 3 hours. After the completion of the reaction, water (116.1 g) was added and the reaction solution was neutralized with sodium carbonate at 80 to 90° C. The solution was filtered at room temperature and washed in turn with xylene (116.1 g) and water (116.1 g). The resultant crystal was subjected to reflux washing using acetone (80 g) and then filtered. This operation was repeated three times, followed by drying to obtain 5.8 g of 2-hydroxy-3,6-di-2-methoxyphenylaminocarbonylnaphthalene as a white powdered crystal (melting point: 206–210° C.).

Figure 5:
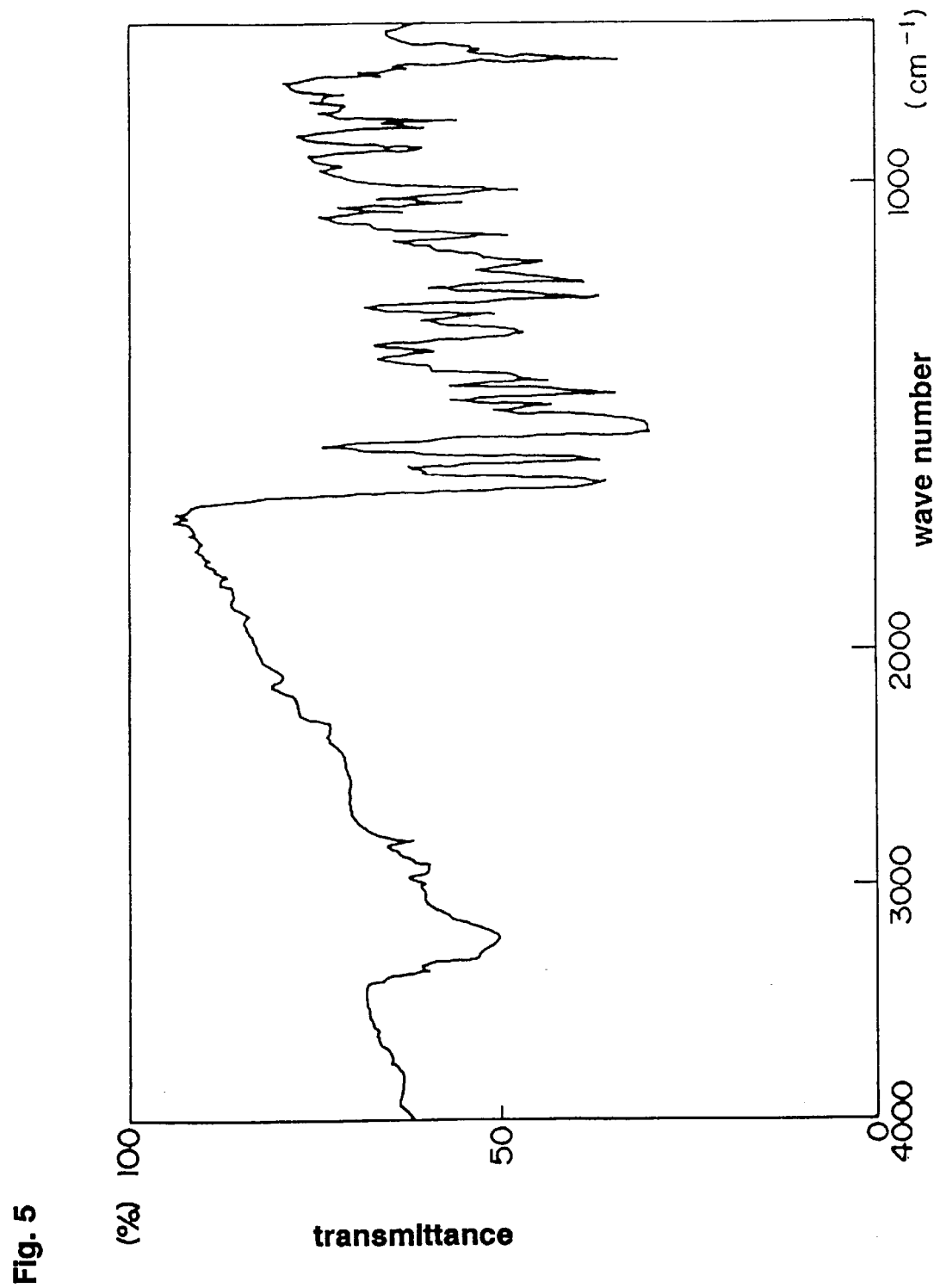
FIG. 5 is a graph illustrating an infrared absorption spectrum of the compound obtained in Example 5.

An infrared spectrum (KBr method) of this compound is shown in FIG. 5.

EXAMPLE 6

Synthesis of 2-hydroxy-3,6-dichlorocarbonylnaphthalene

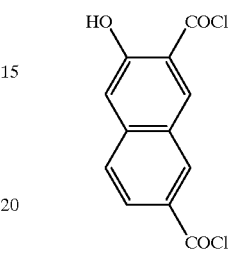

After 2-hydroxy-3,6-dihydroxycarbonylnaphthalene (24.0 g) and dimethylformamide (0.08 g) were added in xylene (410 g), thionyl chloride (66.2 g) was added dropwise at 20° C. over 60 minutes. The mixture was heated to 70° C. and then reacted for 21 hours. Then, xylene and excess thionyl chloride were distilled off under reduced pressure to obtain 28.6 g of an acid chloride.

Figure 6:
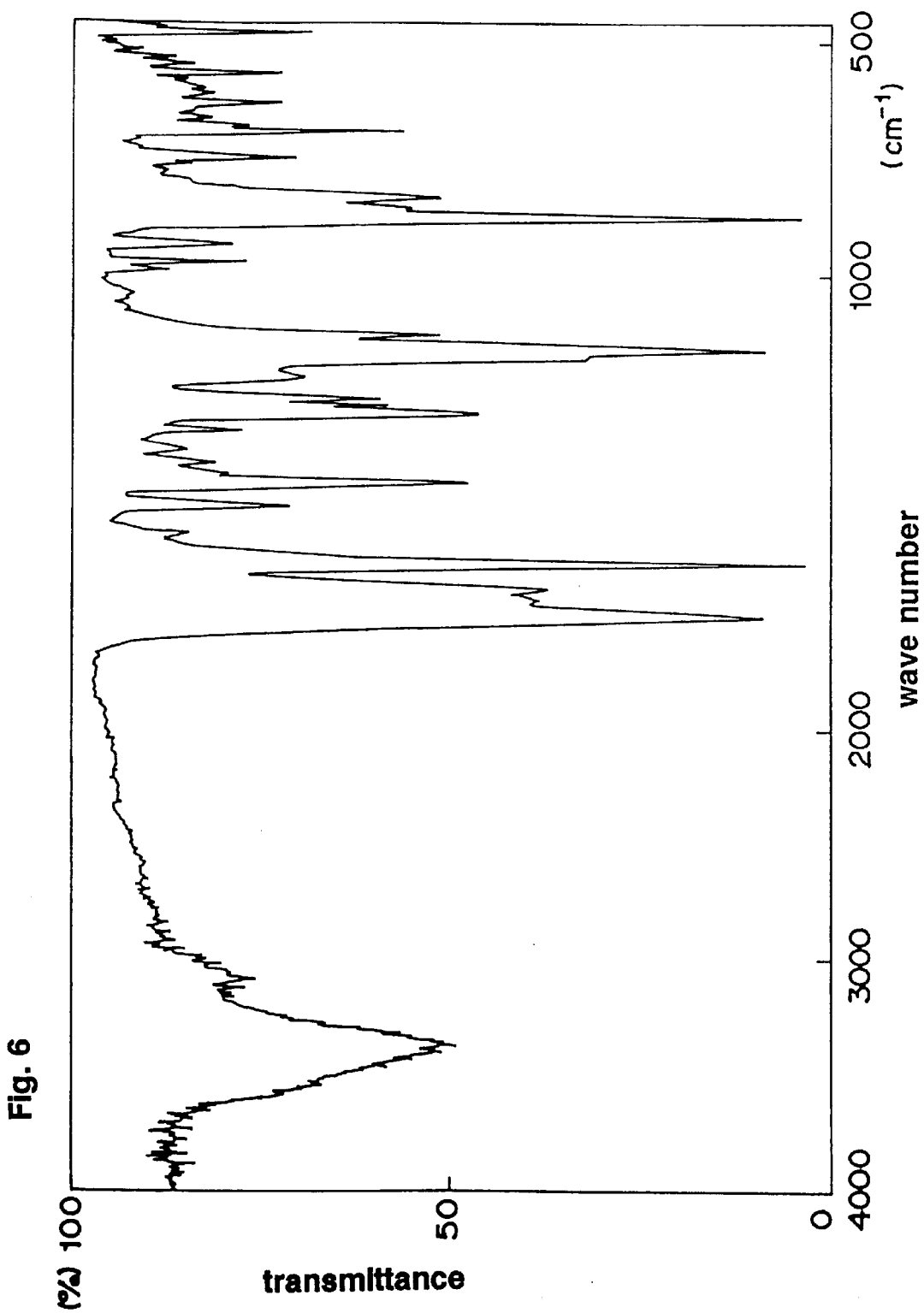
FIG. 6 is a graph illustrating an infrared absorption spectrum of the compound obtained in Example 6.

An infrared spectrum (KBr method) of this compound is shown in FIG. 6.

EXAMPLE 7

Synthesis of 2-hydroxy-3,6-di-2-chlorophenylureidocarbonylnaphthalene

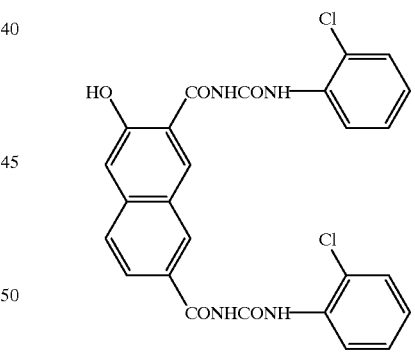

(1) Synthesis of o-chlorophenylurea

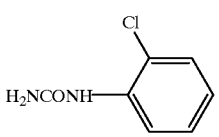

O-chloroaniline (50 g) was added in water (400 g) and acetic acid (200 g), followed by cooling to 15° C. Then, a solution of potassium cyanate (63.6 g) and water (300 g) was added dropwise at not more than 15° C. over 40 minutes. The mixture was heated to 30° C., filtered and then washed with cold water to obtain a white crystal. This crystal was recrystallized from a solution of ethanol (350 g) and water (100 g) to obtain 47.1 g of o-chlorophenylurea as a white needle crystal.

(2) Synthesis of 2-hydroxy-3,6-di-2-chlorophenylureidocarbonylnaphthalene

The acid chloride prepared according to the process of Example 6, i.e. 2-hydroxy-3,6-dichlorocarbonylnaphthalene (5.9 g) was gradually added to a suspension of the o-chlorophenylurea (7.5 g) obtained above and toluene (150 g) at 20° C. After pyridine (3.5 g) was added, the mixture was heated to 90° C. and reacted for 16 hours. Then, the reaction solution was cooled to 15° C. and filtered. The resultant product was subjected to reflux washing for 5 hours using acetone (100 g), filtered and then dried to obtain 8.8 g of 2-hydroxy-3,6-di-2-chlorophenylureidocarbonylnaphthalene as a pale yellow powdered crystal (melting point: 213.2–222.4° C.).

Figure 7:
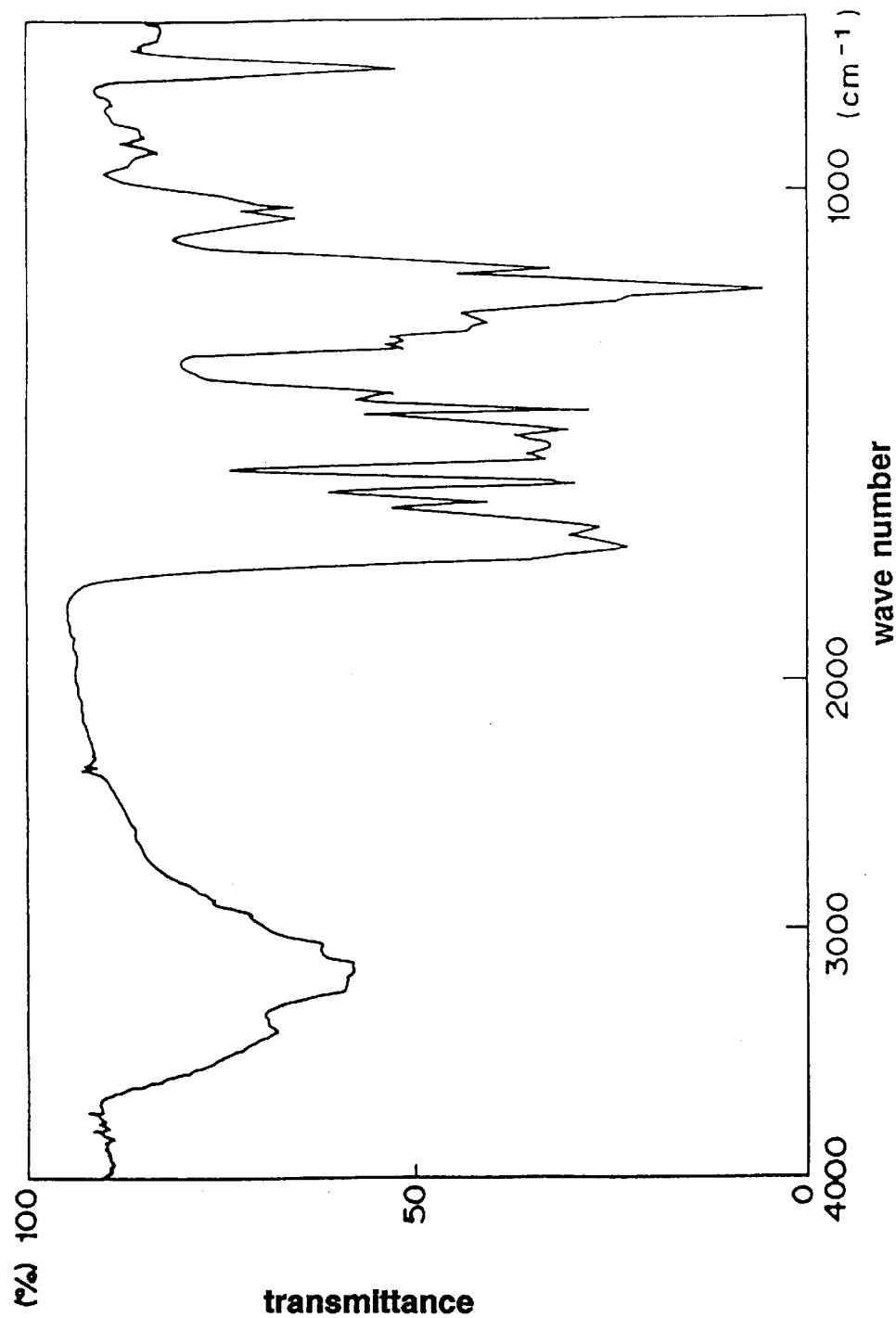
FIG. 7 is a graph illustrating an infrared absorption spectrum of the compound obtained in Example 7.

An infrared spectrum (KBr method) of this compound is shown in FIG. 7.

EXAMPLE 8

Synthesis of 2-hydroxy-3,6-di-4-Phenoxyphenylaminocarbonylnaphthalene

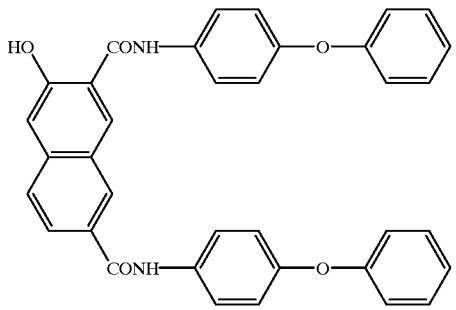

To a solution of 4-aminodiphenyl ether (11.2 g), N-methyl-2-pyrrolidone (75.5 g) and toluene (30.2 g) was gradually added the acid chloride (5.5 g) obtained in Example 6, and then the mixture was heated to 90° C. and reacted for 25 hours. After the reaction solution was cooled to 25° C. and filtered, toluene was distilled off under reduced pressure. Then, the solution was crystallized by using methanol (158.1 g) and filtered. The resultant product was subjected to reflux washing using methanol (200.0 g) for 1 hour, filtered and then dried to obtain 9.2 g of 2-hydroxy-3,6-di-4-phenoxyphenylaminocarbonylnaphthalene as a pale beige powdered crystal (DSC analysis value: 314.8° C.).

Figure 8:
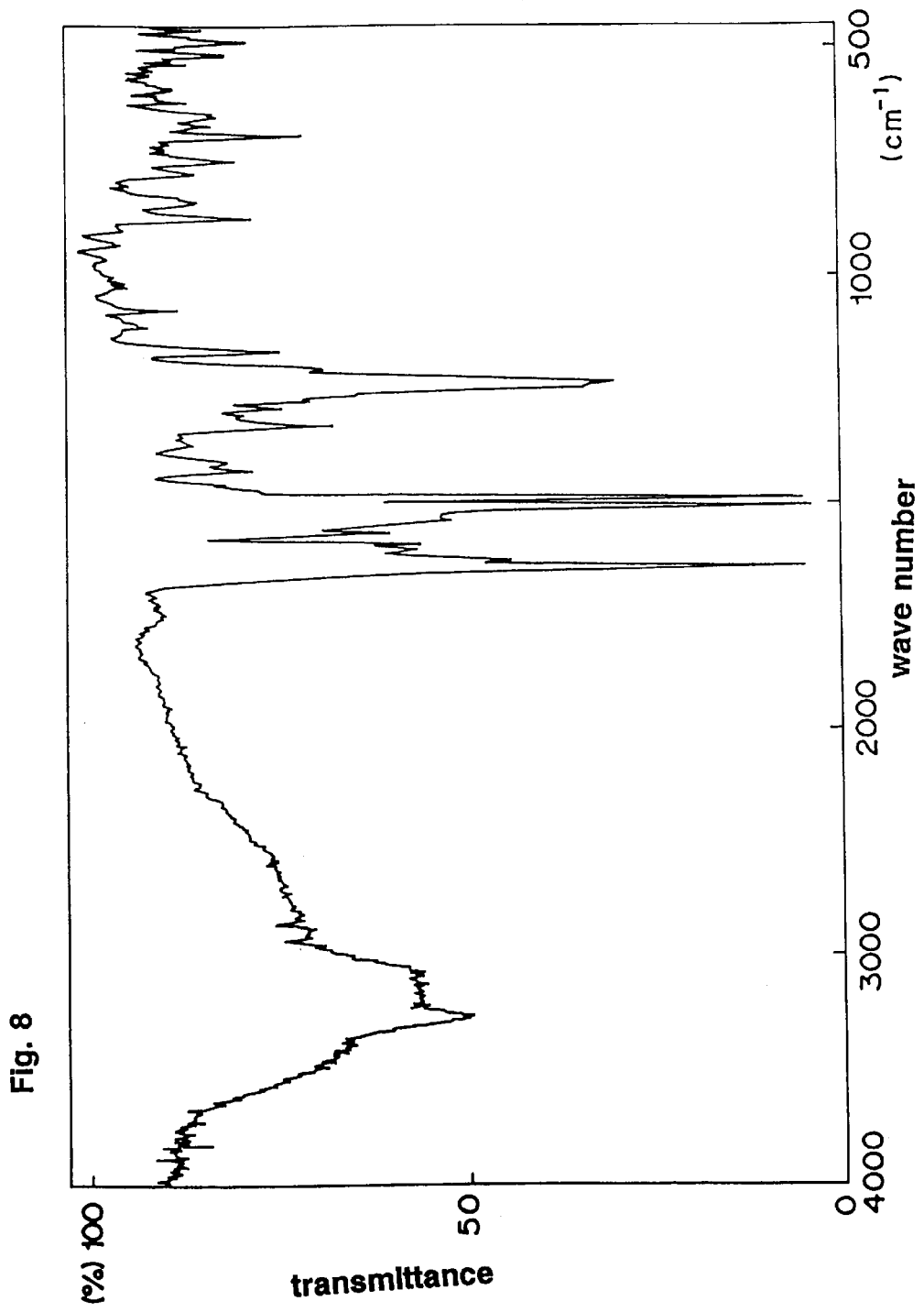
FIG. 8 is a graph illustrating an infrared absorption spectrum of the compound obtained in Example 8.

An infrared spectrum (KBr method) of this compound is shown in FIG. 8.

EXAMPLE 9

Synthesis of 2-hydroxy-3,6-di-anthraquinone-2-yl-aminocarbonylnaphthalene

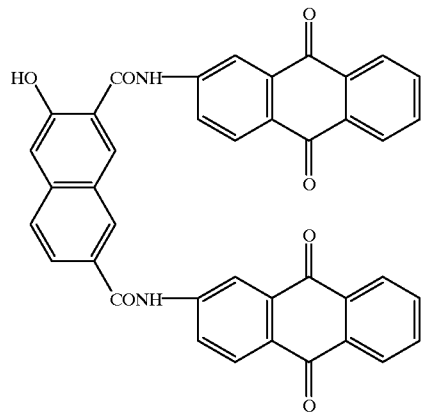

2-Aminoanthraquinone (14.5 g), N-methyl-2-pyrrolidone (145.6 g) and toluene (40.0 g) were dissolved by heating to 60° C. and the acid chloride (5.5 g) obtained in Example 6 was gradually added, and then the mixture was amidated according to Example 8. After the reaction solution was cooled to 25° C. and filtered, toluene was distilled off under reduced pressure. Then, the solution was crystallized by using methanol (244.3 g). The resultant product was subjected to reflux washing using acetone (320.2 g) for 1 hour, filtered and then dried to obtain 11.0 g of 2-hydroxy-3,6-di-anthraquinone-2-yl-aminocarbonylnaphthalene as an olive powdered crystal (DSC analysis value: 367.2° C.).

Figure 9:
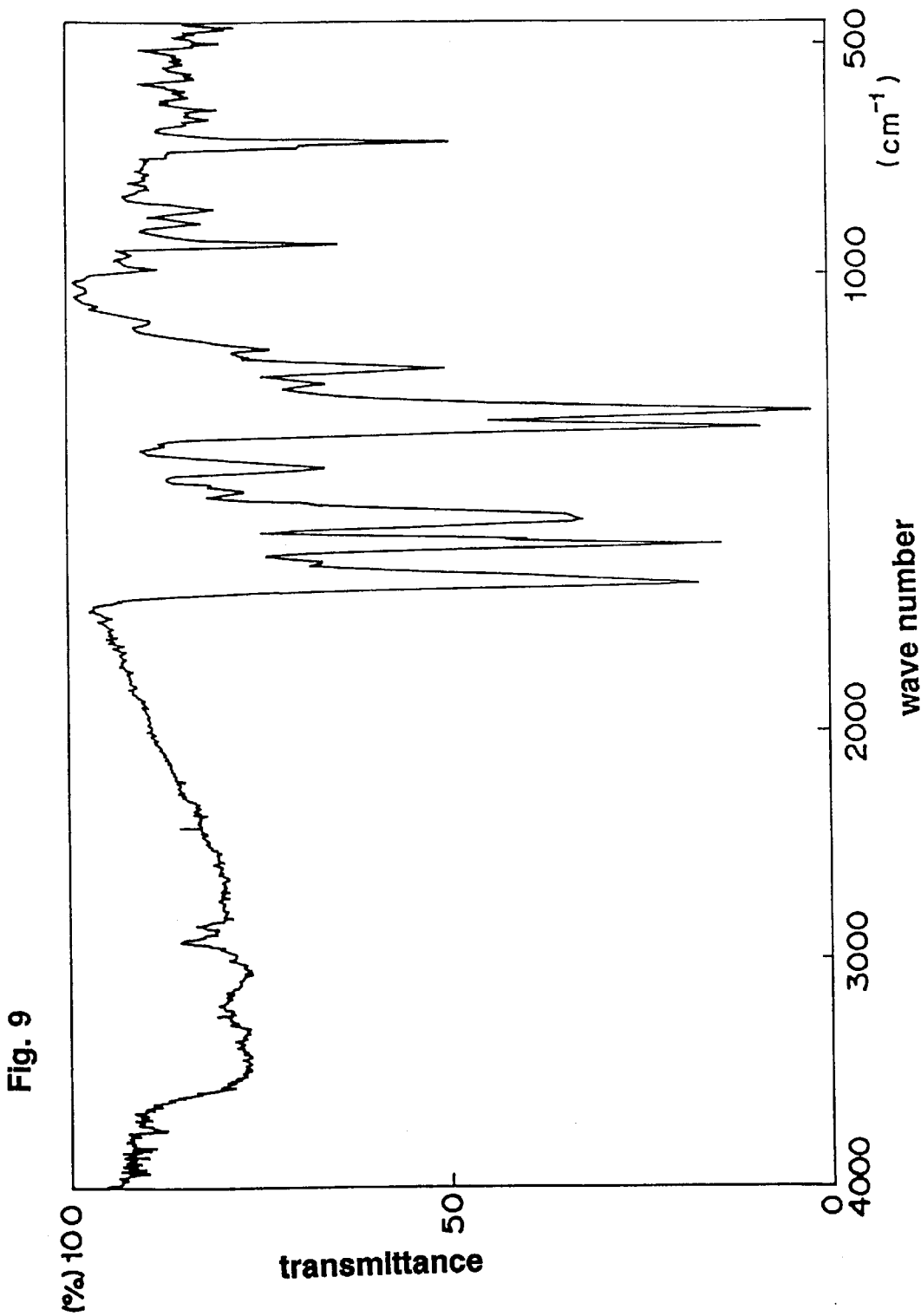
FIG. 9 is a graph illustrating an infrared absorption spectrum of the compound obtained in Example 9.

An infrared spectrum (KBr method) of this compound is shown in FIG. 9.

EXAMPLE 10

Synthesis of 2-hydroxy-3,6-bis(2,5-dimethoxy-4-benzoylaminophenyl-aminocarbonyl)naphthalene

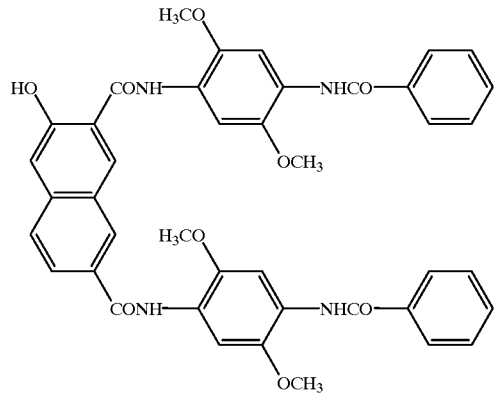

2,5-Dimethoxy-4-benzoylaminoaniline (16.6 g), N-methyl-2-pyrrolidone (111.2 g) and toluene (30.1 g) were dissolved at room temperature and the acid chloride (5.5 g) obtained in Example 6 was gradually added, and then the mixture was amidated according to Example 8. After the reaction solution was cooled to 25° C. and filtered, toluene was distilled off under reduced pressure. Then, the solution was crystallized by using methanol (377.2 g). The resultant product was subjected to reflux washing using methanol (250.0 g) for 1 hour, filtered and then dried to obtain 12.4 g of 2-hydroxy-3,6-bis(2,5-dimethoxy-4-benzoylaminophenyl-aminocarbonyl)naphthalene as a dull yellow powdered crystal (DSC analysis value: 327.4° C.).

Figure 10:
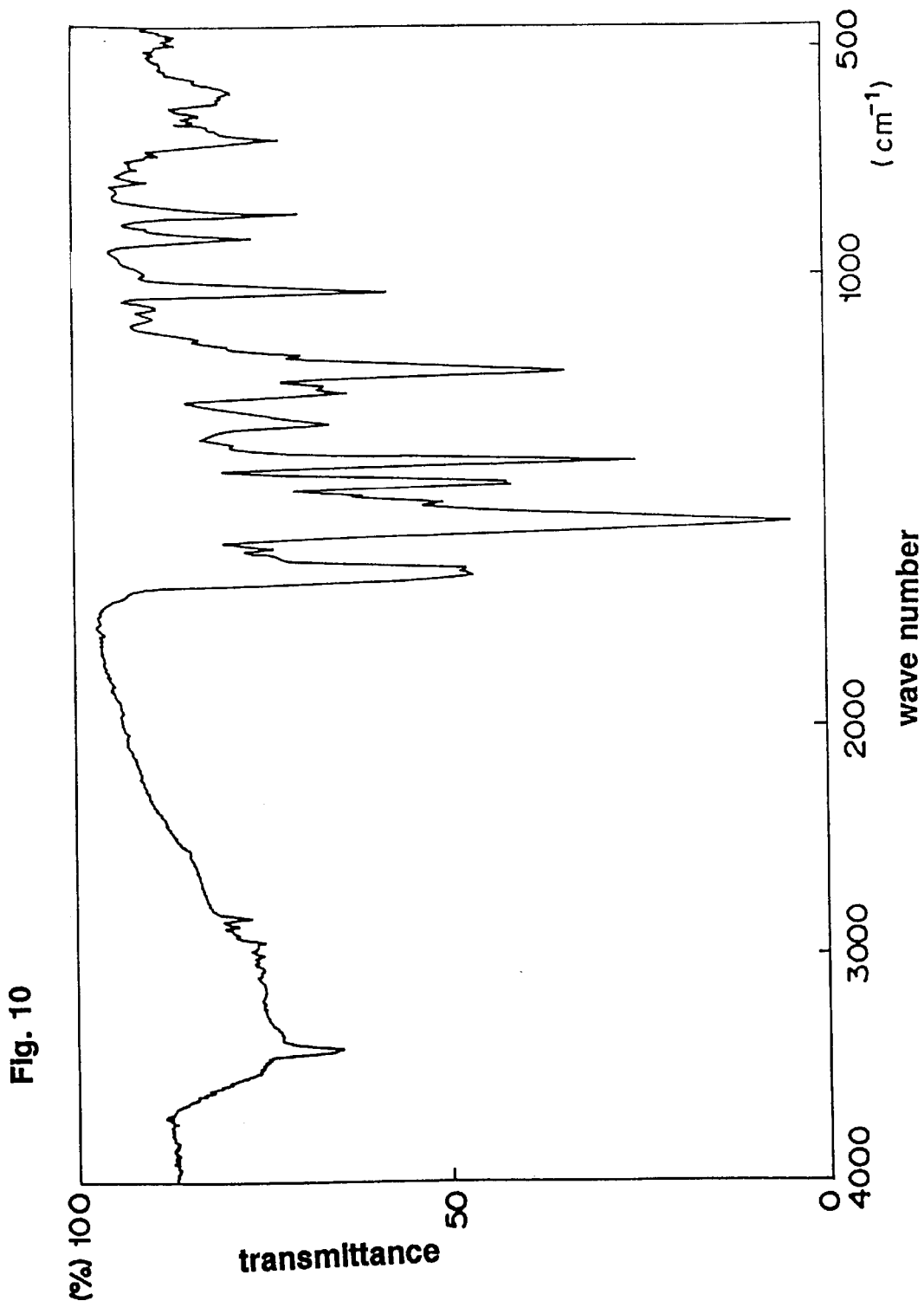
FIG. 10 is a graph illustrating an infrared absorption spectrum of the compound obtained in Example 10.

An infrared spectrum (KBr method) of this compound is shown in FIG. 10.

EXAMPLE 11

Synthesis of 2-hydroxy-3,6-di-2-methoxycarbonylphenyl-aminocarbonylnaphthalene

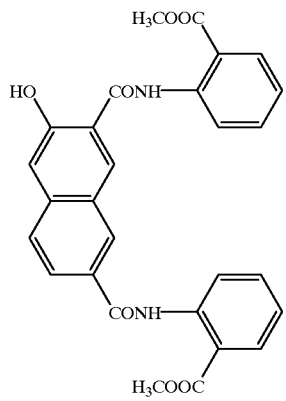

Methyl-2-aminobenzoate (9.3 g), N-methyl-2-pyrrolidone (169.8 g) and toluene (136.0 g) were dissolved at room temperature and the acid chloride (5.5 g) obtained in Example 6 was gradually added, and then the mixture was amidated at 90° C. for 22 hours. After the reaction solution was cooled to 25° C. and filtered, toluene was distilled off under reduced pressure. Then, the solution was crystallized by using methanol (226.7 g). The resultant product was subjected to reflux washing using methanol (199.4 g) for 1 hour, filtered and then dried to obtain 8.0 g of 2-hydroxy-3,6-di-2-methoxycarbonylphenyl-aminocarbonylnaphthalene as a light yellow powdered crystal (DSC analyswas value: 239.6° C.).

Figure 11:
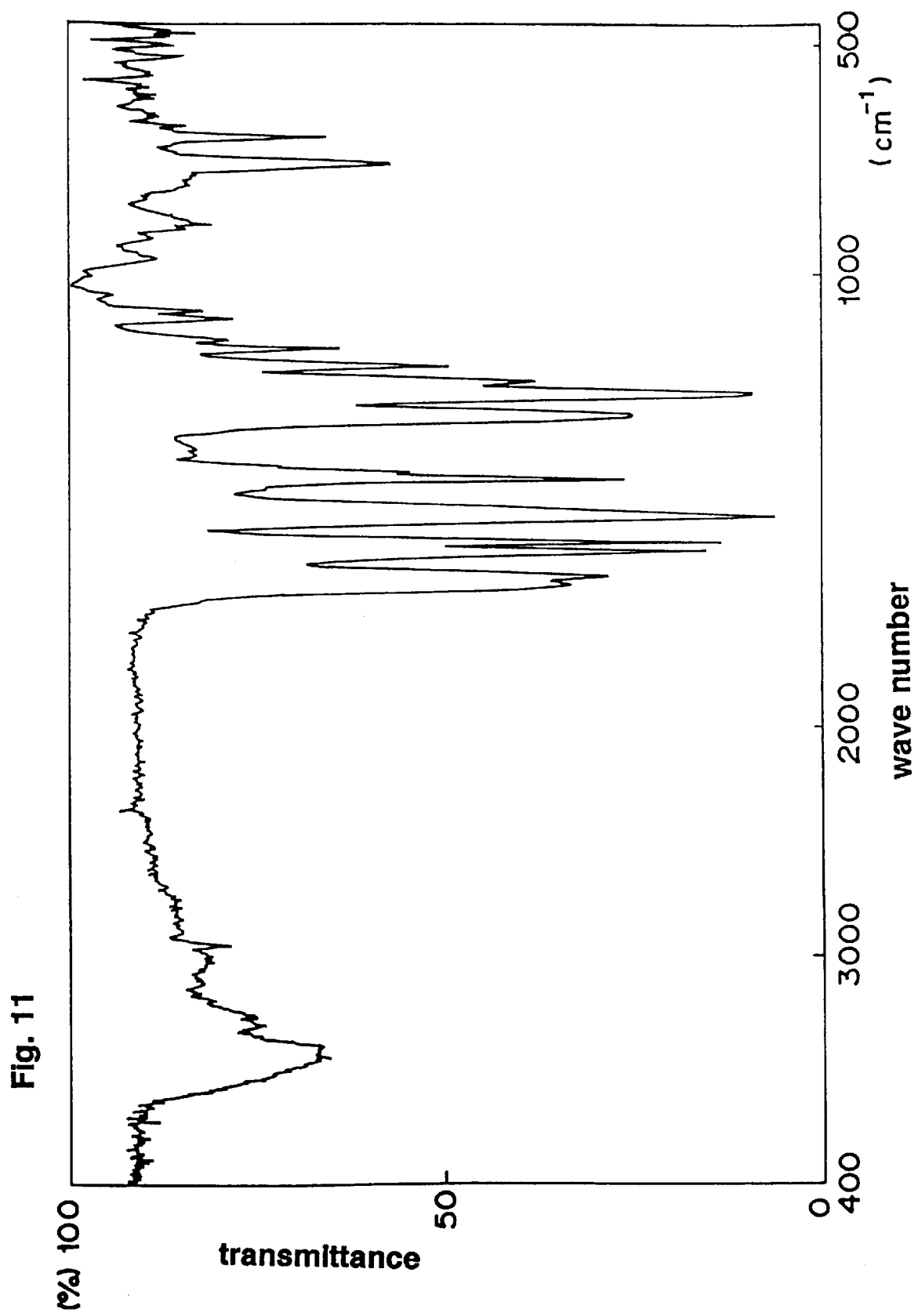
FIG. 11 is a graph illustrating an infrared absorption spectrum of the compound obtained in Example 11.

An infrared spectrum (KBr method) of thwas compound is shown in FIG. 11.

EXAMPLE 12

Synthesis of 2-hydroxy-3,6-bis(2-methoxy-5-diethylaminosulfonyl-aminocarbonyl)naphthalene

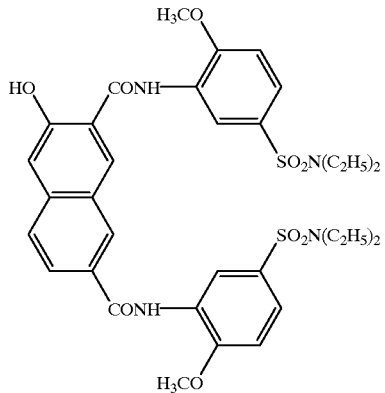

3-Amino-4-methoxydiethylaminosulfonylbenzene (15.6 g), N-methyl-2-pyrrolidone (86.1 g) and toluene (34.3 g) were dissolved at room temperature and the acid chloride (5.4 g) obtained in Example 6 was gradually added, and then the mixture was amidated at 90° C. for 24 hours. After the reaction solution was cooled to 25° C. and filtered, toluene was distilled off under reduced pressure. Then, the solution was crystallized by using methanol (350.1 g). The resultant product was filtered and then dried to obtain 8.9 g of 2-hydroxy-3,6-bis(2-methoxy-5-diethylaminosulfonylphenyl-aminocarbonyl)naphthalene as a cream powdered crystal (DSC analysis value: 245.0° C.).

Figure 12:
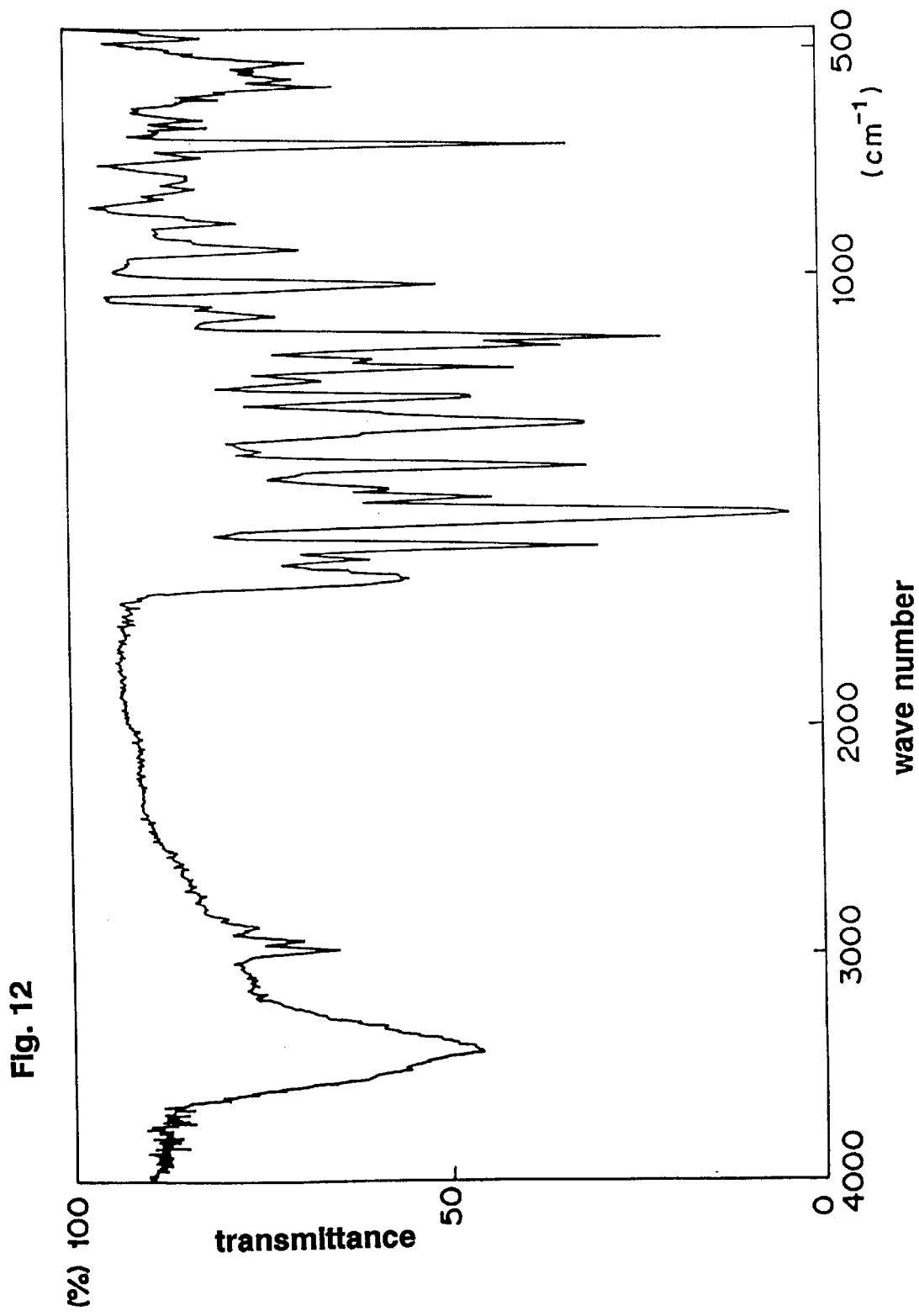
FIG. 12 is a graph illustrating an infrared absorption spectrum of the compound obtained in Example 12.

An infrared spectrum (KBr method) of this compound is shown in FIG. 12.

EXAMPLE 13

Synthesis of 2-hydroxy-3,6-di-benzimidazolon-5-yl-aminocarbonylnaphthalene

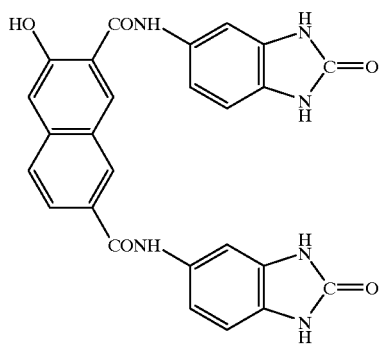

To a solution of 5-aminobenzimidazolone (13.5 g), N-methyl-2-pyrrolidone (99.0 g) and toluene (44.8 g) was gradually added the acid chloride (8.1 g) obtained in Example 6, and then the mixture was amidated at 90° C. for 29 hours. The reaction solution was cooled to 25° C., filtered and then washed with methanol. The resultant crystal was dissolved in N-methyl-2-pyrrolidone (441.9 g) at 120° C. and carborafine (2.1 g) was added, and then the mixture was carbon-treated at 120° C. for 1 hour. After carbon was removed by filtration, the solution was cooled and crystallized by using methanol (146.4 g). The resultant product was filtered and then dried to obtain 11.8 g of 2-hydroxy-3,6-di-benzimidazolon-5-yl-aminocarbonylnaphthalene as a yellowish green powdered crystal (DSC analysis value: 421.4° C.).

Figure 13:
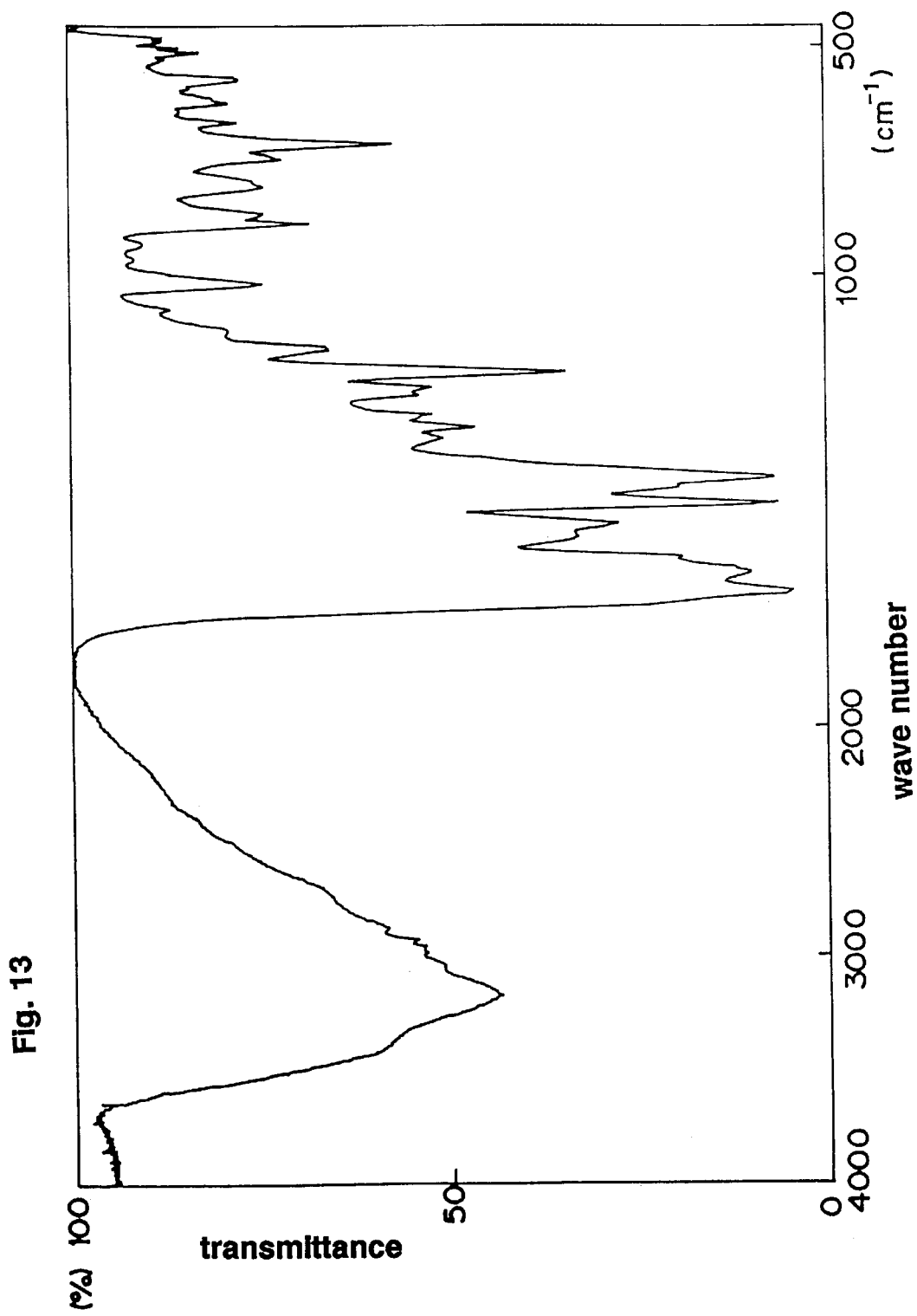
FIG. 13 is a graph illustrating an infrared absorption spectrum of the compound obtained in Example 13.

An infrared spectrum (KBr method) of this compound is shown in FIG. 13.

EXAMPLE 14

Synthesis of 2-hydroxy-3,6-di-3-nitrophenylaminocarbonylnaphthalene

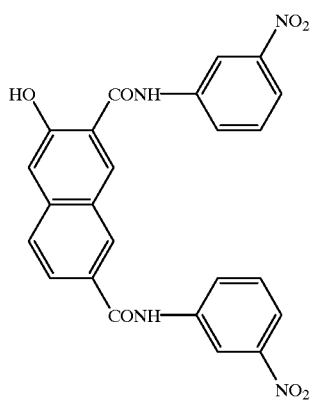

m-Nitroaniline (8.38 g), N-methyl-2-pyrrolidone (65.5 g) and toluene (30.3 g) were dissolved at room temperature and the acid chloride (5.5 g) obtained in Example 6 was gradually added, and then the mixture was amidated at 90° C. for 24 hours. After the reaction solution was cooled to 25° C. and filtered, toluene was distilled off under reduced pressure. Then, the solution was crystallized by using methanol (197.3 g), filtered and dried. The resultant product was subjected to reflux washing using methanol (263.4 g) for 1 hour, filtered and then dried to obtain 7.8 g of 2-hydroxy-3,6-di-3-nitrophenylaminocarbonylnaphthalene as a cream powdered crystal (DSC analysis value: 342.9° C.).

Figure 14:
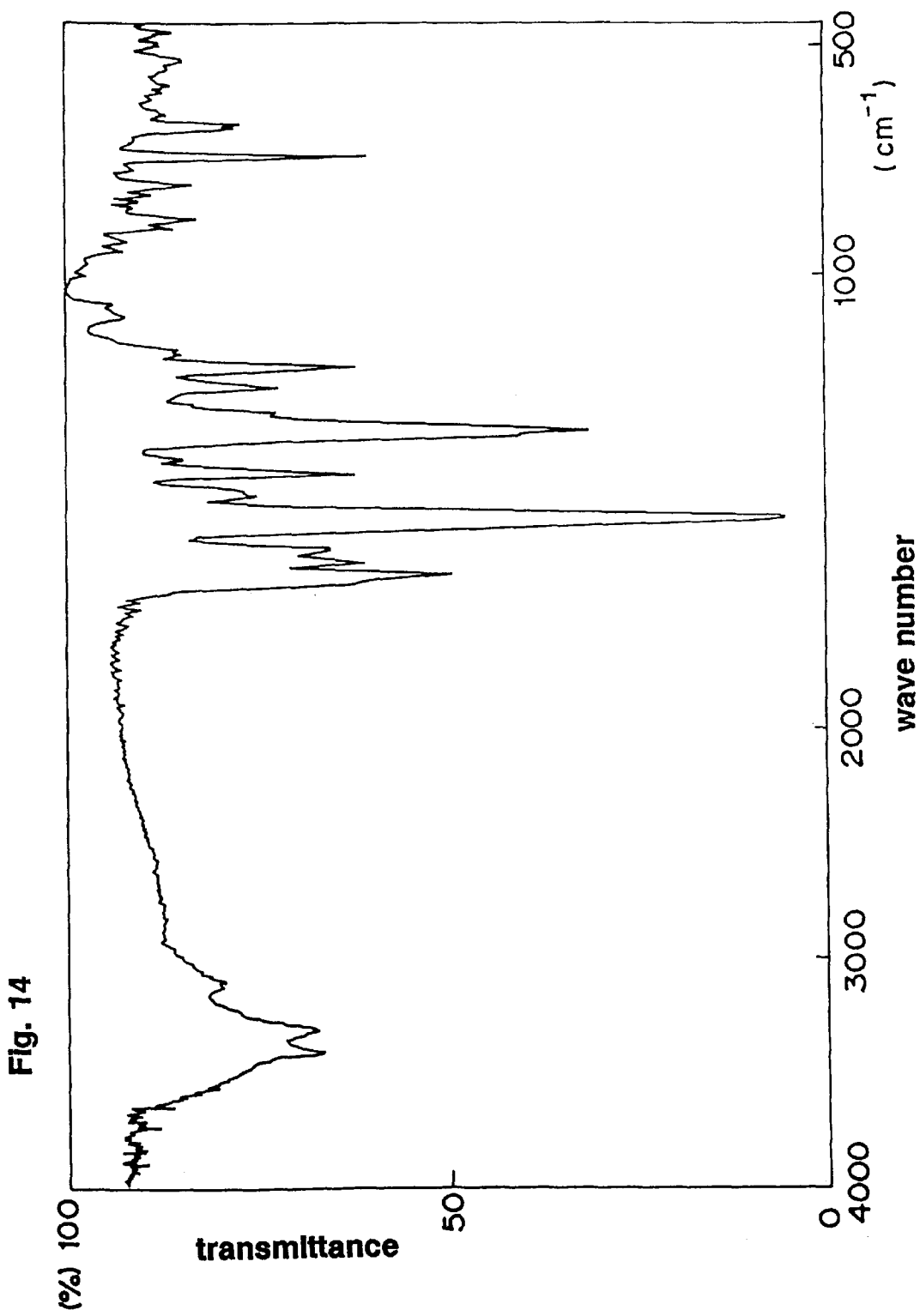
FIG. 14 is a graph illustrating an infrared absorption spectrum of the compound obtained in Example 14.

An infrared spectrum (KBr method) of this compound is shown in FIG. 14.

EXAMPLE 15

Synthesis of 2-hydroxy-3,6-di-9-ethylcarbazol-3-yl-aminocarbonylnaphthalene

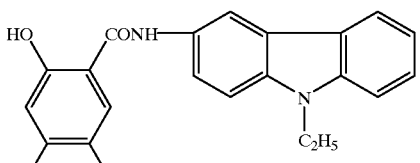
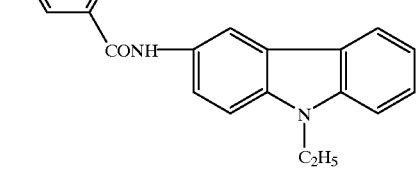

3-Amino-9-ethylcarbazole (12.8 g), N-methyl-2-pyrrolidone (65.6 g) and toluene (30.4 g) were dissolved at room temperature and the acid chloride (4.1 g) obtained in Example 6 was gradually added, and then the mixture was amidated at 90° C. for 23 hours. After the reaction solution was cooled to 25° C. and filtered, toluene was distilled off under reduced pressure. Then, the solution was crystallized by using methanol (422.9 g) and filtered, and the resultant crystal was subjected to reflux washing using methanol (200.5 g) for 1 hour, filtered and dried. The resultant product was dissolved in N-methyl-2-pyrrolidone (90.4 g) at 120° C. and carborafine (1.0 g) was added, and then the mixture was carbon-treated at 120° C. for 1 hour. After carbon was removed by filtration, the solution was cooled and crystallized by using methanol (301.8 g). The resultant product was filtered and then dried to obtain 3.7 g of 2-hydroxy-3,6-di-9-ethylcarbazol-3-yl-aminocarbonylnaphthalene as a grayish yellowgreen powdered crystal (TG decomposition point: 417.2° C.).

Figure 15:
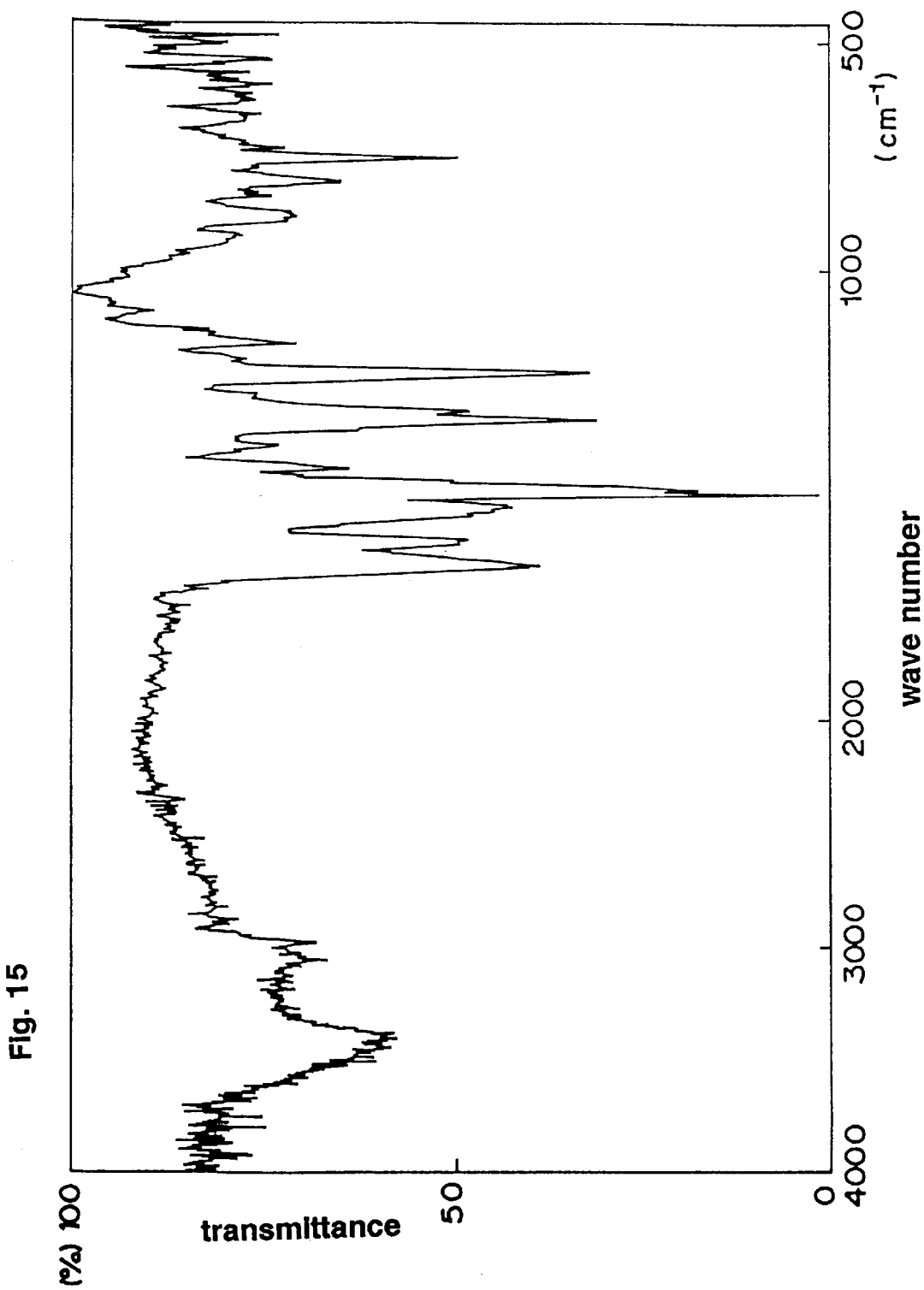
FIG. 15 is a graph illustrating an infrared absorption spectrum of the compound obtained in Example 15.

An infrared spectrum (KBr method) of this compound is shown in FIG. 15.

EXAMPLE 16

Synthesis of 2-hydroxy-3,6-bis(3-trifluoromethylphenyl-aminocarbonyl)naphthalene

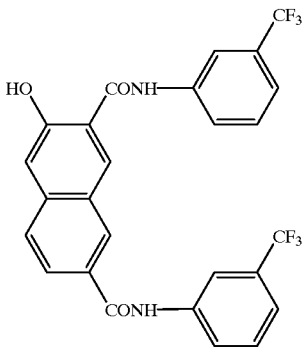

3-Aminotrifluoromethylbenzene (9.7 g), N-methyl-2-pyrrolidone (65.2 g) and toluene (30.0 g) were dissolved at room temperature and the acid chloride (5.5 g) obtained in Example 6 was gradually added, and then the mixture was amidated at 90° C. for 24 hours. The reaction solution was dried under reduced pressure, dissolved in methyl ethyl ketone (317.4 g) and then washed three times with aqueous 8% hydrochloric acid (167.1 g). The solution was crystallized by using water (418.2 g), filtered and then dried. The product was dissolved in N-methyl-2-pyrrolidone (56.8 g) at 120° C. and carborafine (0.8 g) was added, and then the mixture was carbon-treated at 120° C. for 1 hour. After carbon was removed by filtration, the solution was cooled and crystallized by using water (164.6 g) and then filtered. The resultant product was dissolved in ethyl acetate (202.1 g) and xylene (123.6 g) was added, and then the mixture was concentrated, cooled and crystallized. The resultant product was filtered and then dried to obtain 4.9 g of 2-hydroxy-3, 6-bis(3-trifluoromethylphenylaminocarbonyl)naphthalene as a pale beige powdered crystal (TG decomposition point: 256.4° C.).

Figure 16:
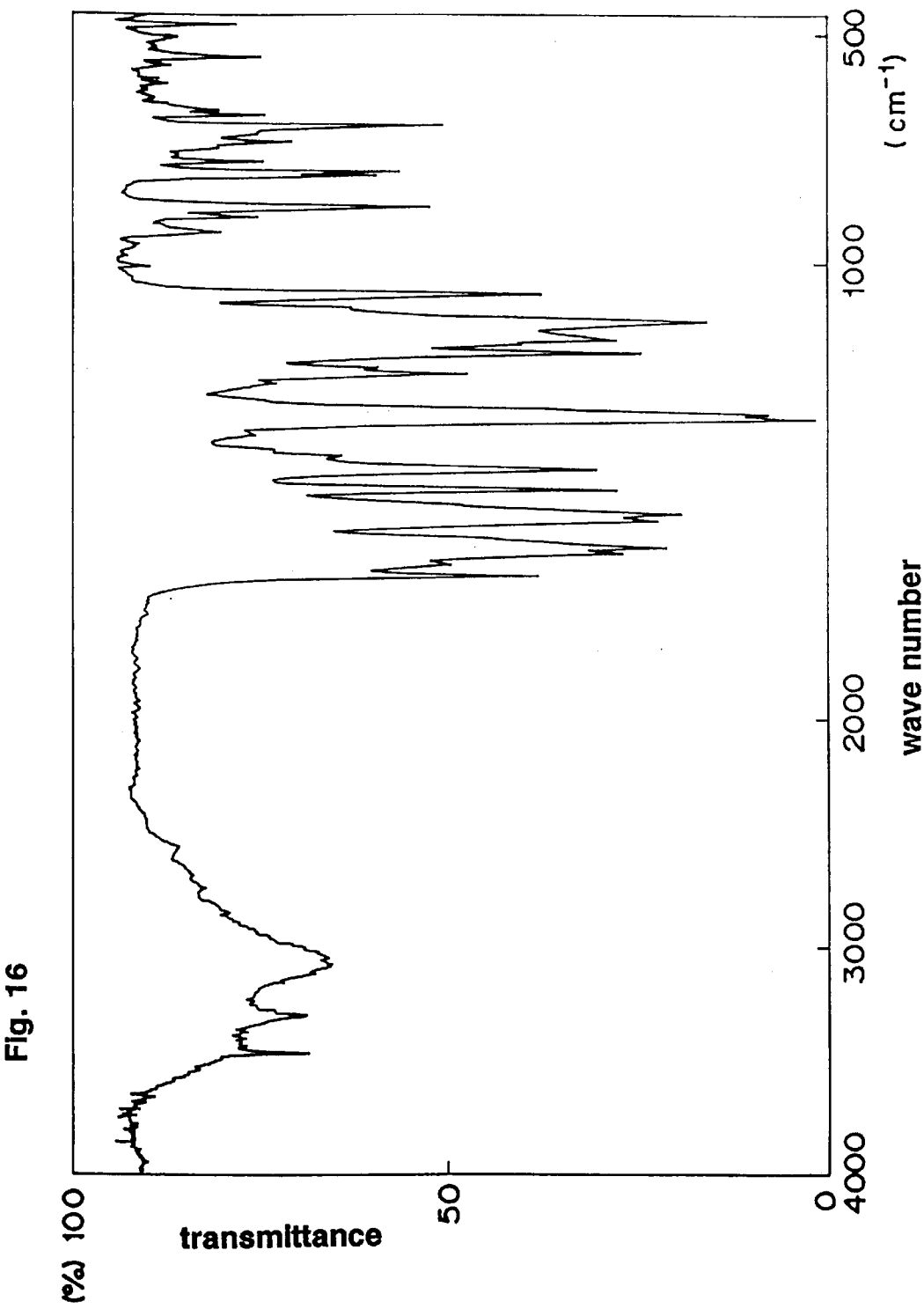
FIG. 16 is a graph illustrating an infrared absorption spectrum of the compound obtained in Example 16.

An infrared spectrum (KBr method) of this compound is shown in FIG. 16.

EXAMPLE 17

Synthesis of 2-hydroxy-3,6-di-1-naphthylaminocarbonylnaphthalene

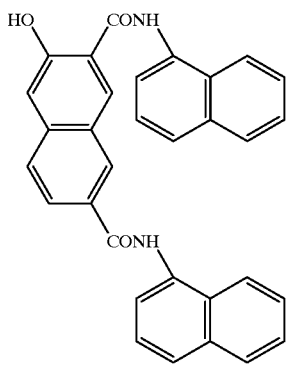

1-Napahthylamine (8.6 g), N-methyl-2-pyrrolidone (60.0 g) and toluene (30.0 g) were dissolved at room temperature and the acid chloride (5.5 g) obtained in Example 6 was gradually added, and then the mixture was amidated at 90° C. for 20 hours. After the reaction solution was cooled to 25° C. and filtered, toluene was distilled off under reduced pressure. Then, the solution was crystallized by using methanol (209.6 g) and subjected to reflux washing. After the solution was filtered and dried, the resultant product was dissolved in N-methyl-2-pyrrolidone (57.9 g) at 120° C. and carborafine (3.0 g) was added, and then the mixture was carbon-treated at 120° C. for 1 hour. After carbon was removed by filtration, the solution was concentrated, crystallized by using methanol (51.7 g), filtered and then dried to obtain 5.5 g of 2-hydroxy-3,6-di-1-naphthylaminocarbonylnaphthalene as a grayish olive powdered crystal (DSC analysis value: 292.1° C.).

Figure 17:
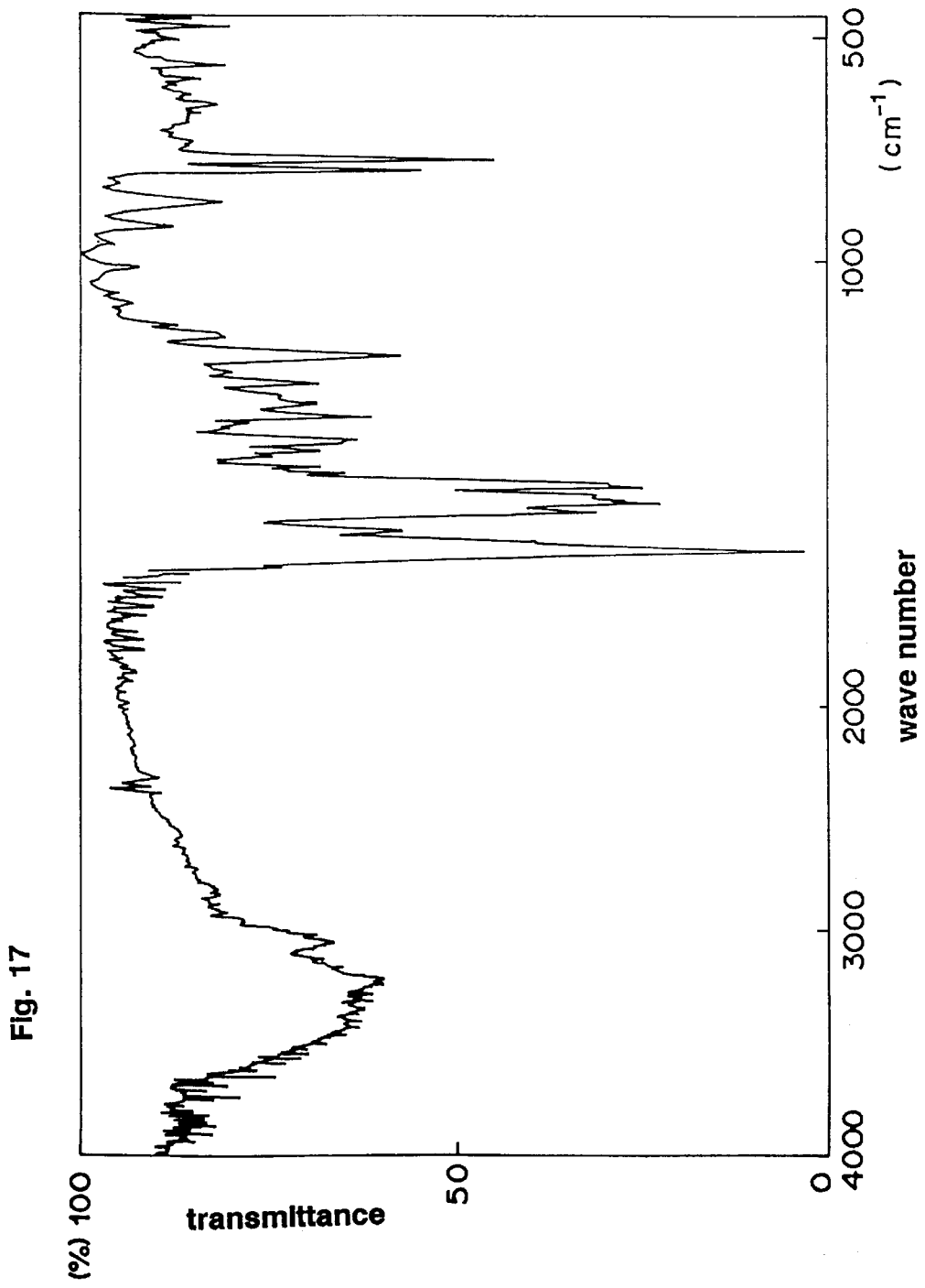
FIG. 17 is a graph illustrating an infrared absorption spectrum of the compound obtained in Example 17.

An infrared spectrum (KBr method) of this compound is shown in FIG. 17.

EXAMPLE 18

Synthesis of 2-hydroxy-3,6-bis (pentafluorophenyl-aminocarbonyl)naphthalene

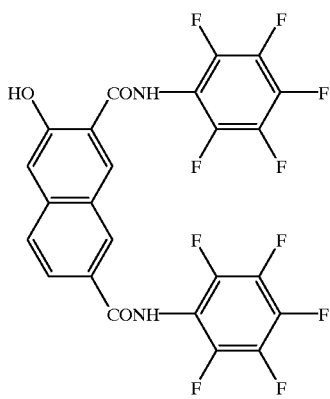

Pentafluoroaniline (9.1 g), N-methyl-2-pyrrolidone (60.1 g) and toluene (30.0 g) were dissolved at room temperature and the acid chloride (4.5 g) obtained in Example 6 was gradually added, and then the mixture was amidated at 50° C. for 21 hours according to Example 8. After the reaction solution was dried under reduced pressure and dissolved in methanol (980.1 g) at the reflux temperature, carborafine (5.0 g) was added and the mixture was carbon-treated for 1 hour. The resultant product was concentrated, cooled, crystallized, filtered and then dried to obtain 2.3 g of 2-hydroxy-3,6-bis(pentafluorophenylaminocarbonyl) naphthalene as a white powdered crystal (TG decomposition point: 305.7° C.).

Figure 18:
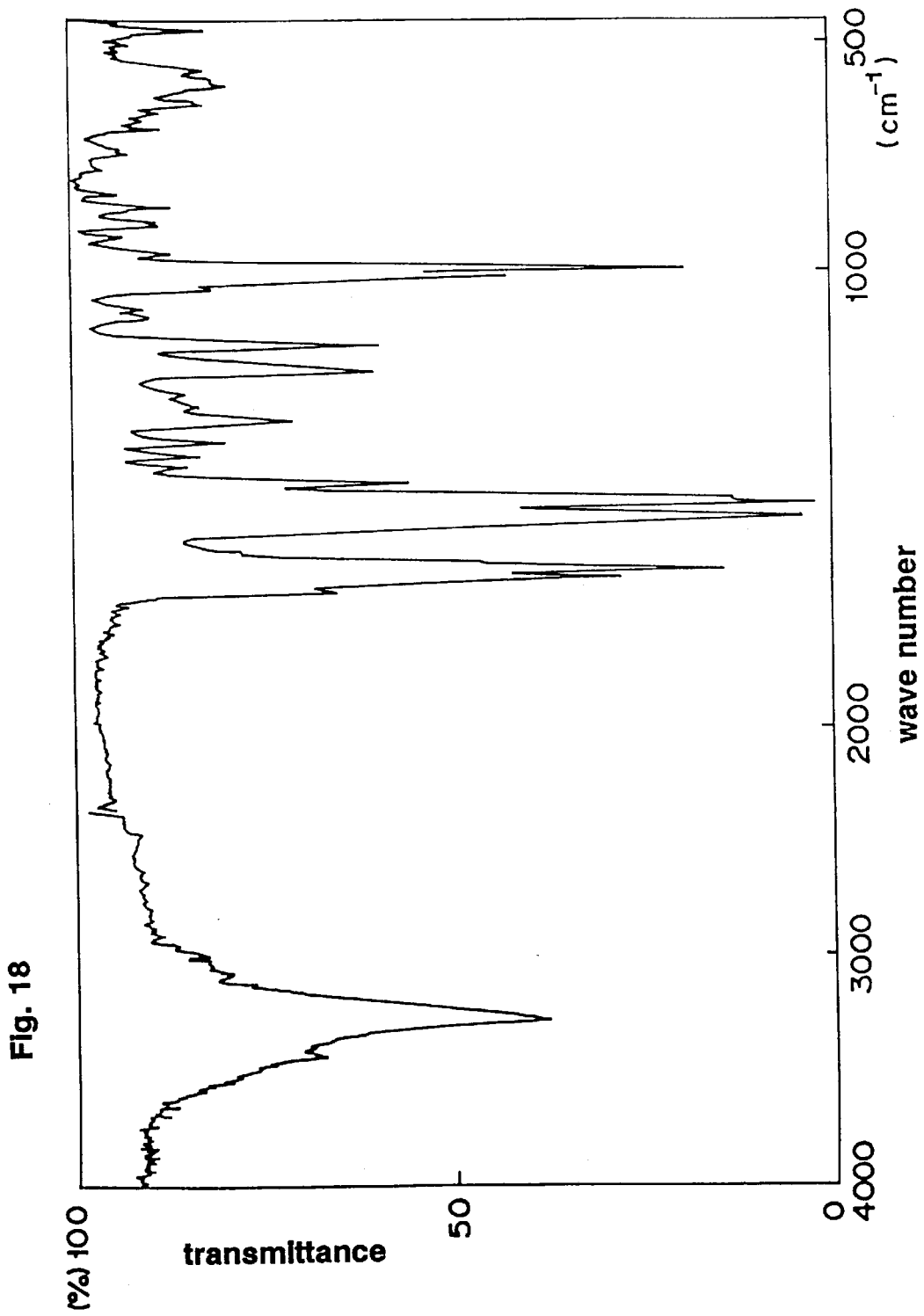
FIG. 18 is a graph illustrating an infrared absorption spectrum of the compound obtained in Example 18.

An infrared spectrum (KBr method) of this compound is shown in FIG. 18.

EXAMPLE 19

Synthesis of 2-benzyloxy-3,6-bis(2,5-dimethoxy-4-benzoylamino-phenylaminocarbonyl)naphthalene

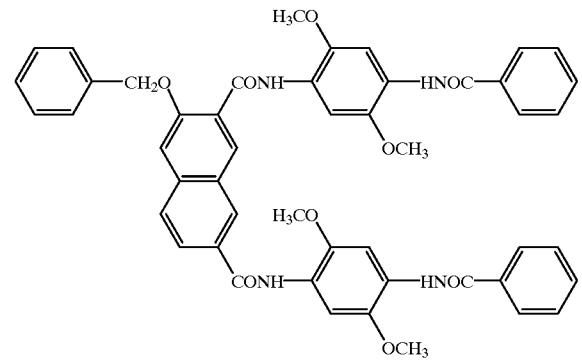

2-Hydroxy-3,6-bis(2,5-dimethoxy-4-benzoylaminophenylaminocarbonyl)naphthalene (2.5 g) obtained in Example 10 was mixed with N,N-dimethylformamide (30 g) and the mixture was dissolved by heating to 100° C. under a nitrogen atmosphere. To the solution, potassium carbonate (0.5 g) was gradually added and benzyl chloride (0.46 g) was added dropwise and the mixed solution was reacted for 5 hours. After the completion of the reaction, the reaction solution was cooled to room temperature, filtered and then washed with water and methanol to obtain 2.65 g of 2-benzyloxy-3,6-bis(2,5-dimethoxy-4-benzoylaminophenylaminocarbonyl)naphthalene as a greenish yellow crystal (DSC analysis value: 282.8° C.)

Figure 19:
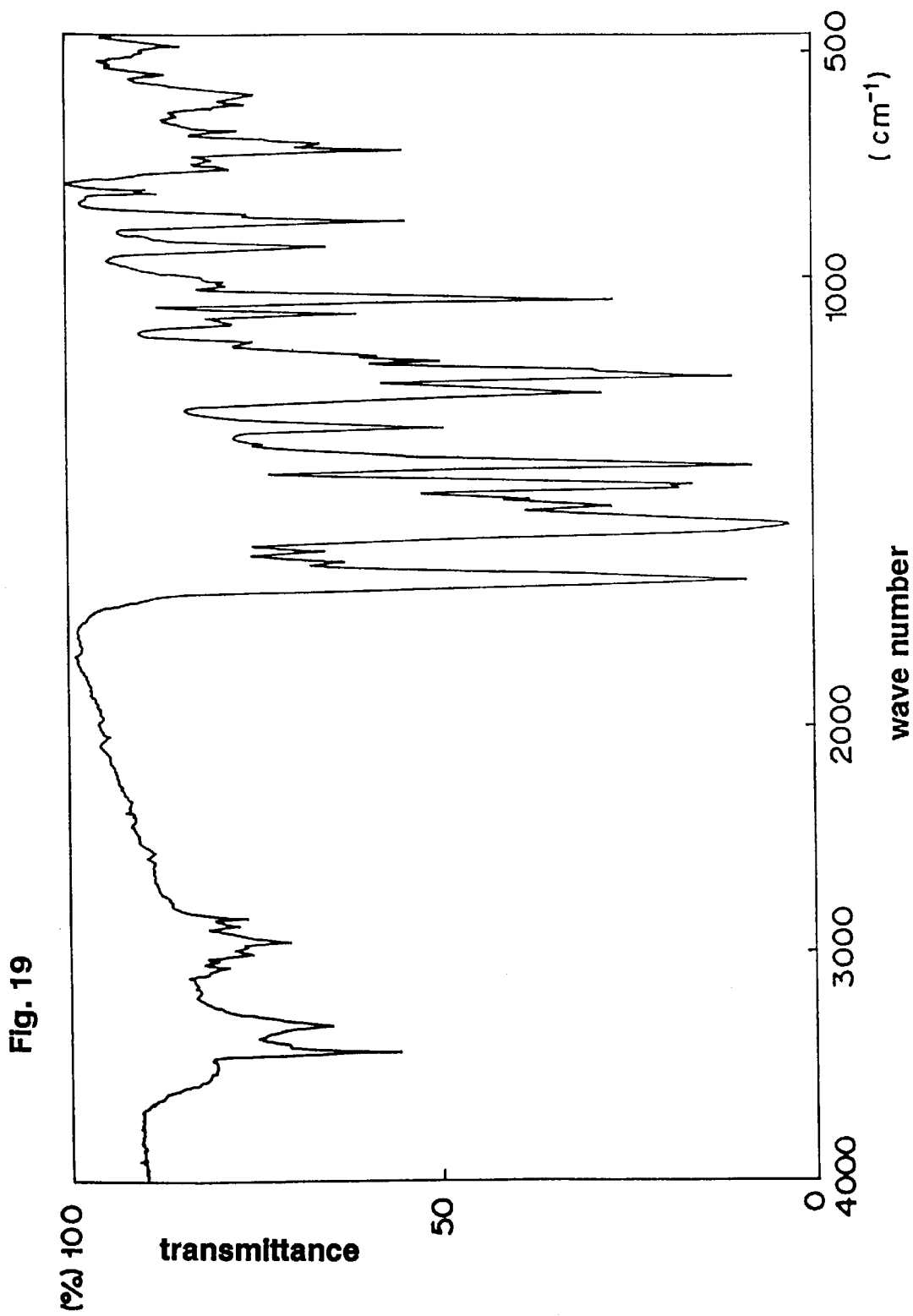
FIG. 19 is a graph illustrating an infrared absorption spectrum of the compound obtained in Example 19.

An infrared spectrum (KBr method) of this compound is shown in FIG. 19.

EXAMPLE 20

Synthesis of 2-ethoxy-3,6-di-4-phenoxyphenylaminocarbonylnaphthalene

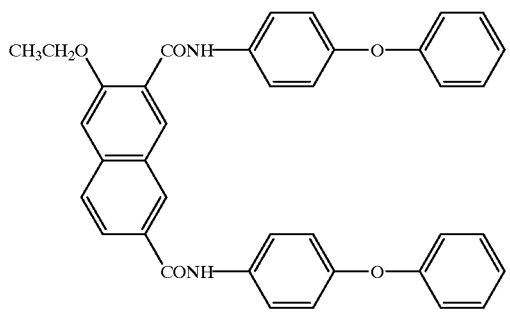

2-Hydroxy-3,6-di-4-phenoxyphenylaminocarbonylnaphthalene (2.83 g) obtained in Example 8 was mixed with N,N-dimethylformamide (30 g) and the mixture was dissolved by heating to 70° C. under a nitrogen atmosphere. To the solution, potassium carbonate (0.38 g) was gradually added and ethyl iodide (0.87 g) was added dropwise and the mixed solution was reacted for 10 hours. After the completion of the reaction, the reaction solution was cooled to room temperature, poured into water (300 g) dropwise, filtered and then washed with water and methanol to obtain 2.81 g of 2-ethoxy-3,6-di-4-phenoxyphenylaminocarbonylnaphthalene as a grayish brown crystal (DSC analysis value: 177.6° C.).

Figure 20:
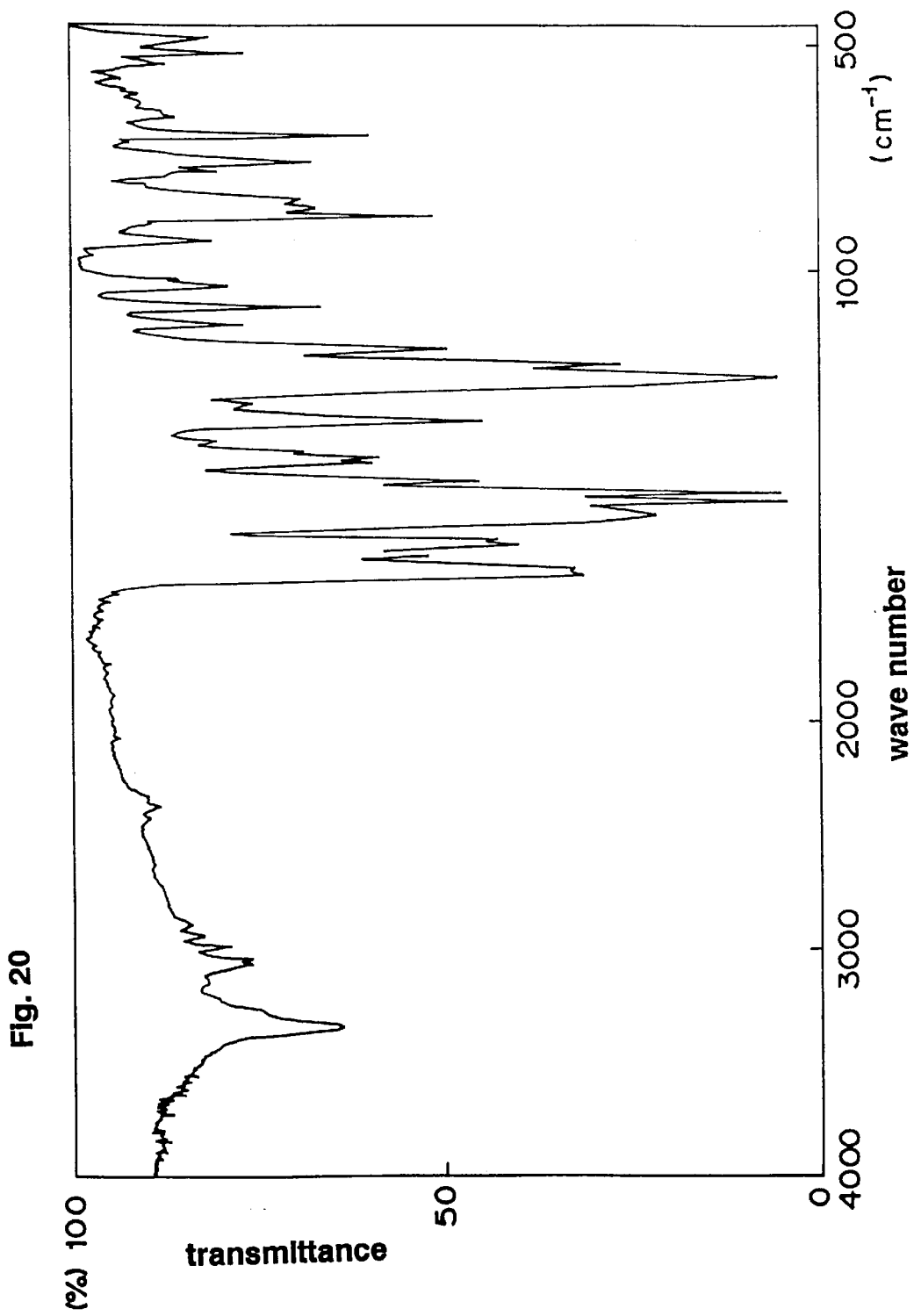
FIG. 20 is a graph illustrating an infrared absorption spectrum of the compound obtained in Example 20.

An infrared spectrum (KBr method) of this compound is shown in FIG. 20.

EXAMPLE 21

Synthesis of 1-bromo-2-hydroxy-3,6-di-3-nitrophenylaminocarbonynaphthalene

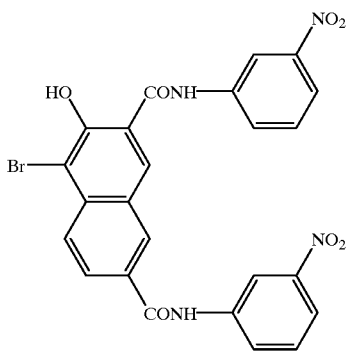

2-Hydroxy-3,6-di-3-nitrophenylaminocarbonylnaphthalene (2.4 g) obtained in Example 14, chloroform (40 g), dimethyl sulfoxide (20 g) and N-methyl-2-pyrrolidone (20 g) were mixed and dissolved. Then, a solution of bromine (0.8 g) and chloroform (10 g) was added dropwise at 5° C. over 1 hour. After the dropwise addition, the mixture was continuously cooled, filtered at 3° C., washed with water and cold methanol and then dried under vacuum to obtain 2.7 g of 1-bromo-2-hydroxy-3,6-di-3-nitrophenylaminocarbonylnaphthalene as a whitish yellow powdered crystal (DSC analysis value: 325.3° C.).

Figure 21:
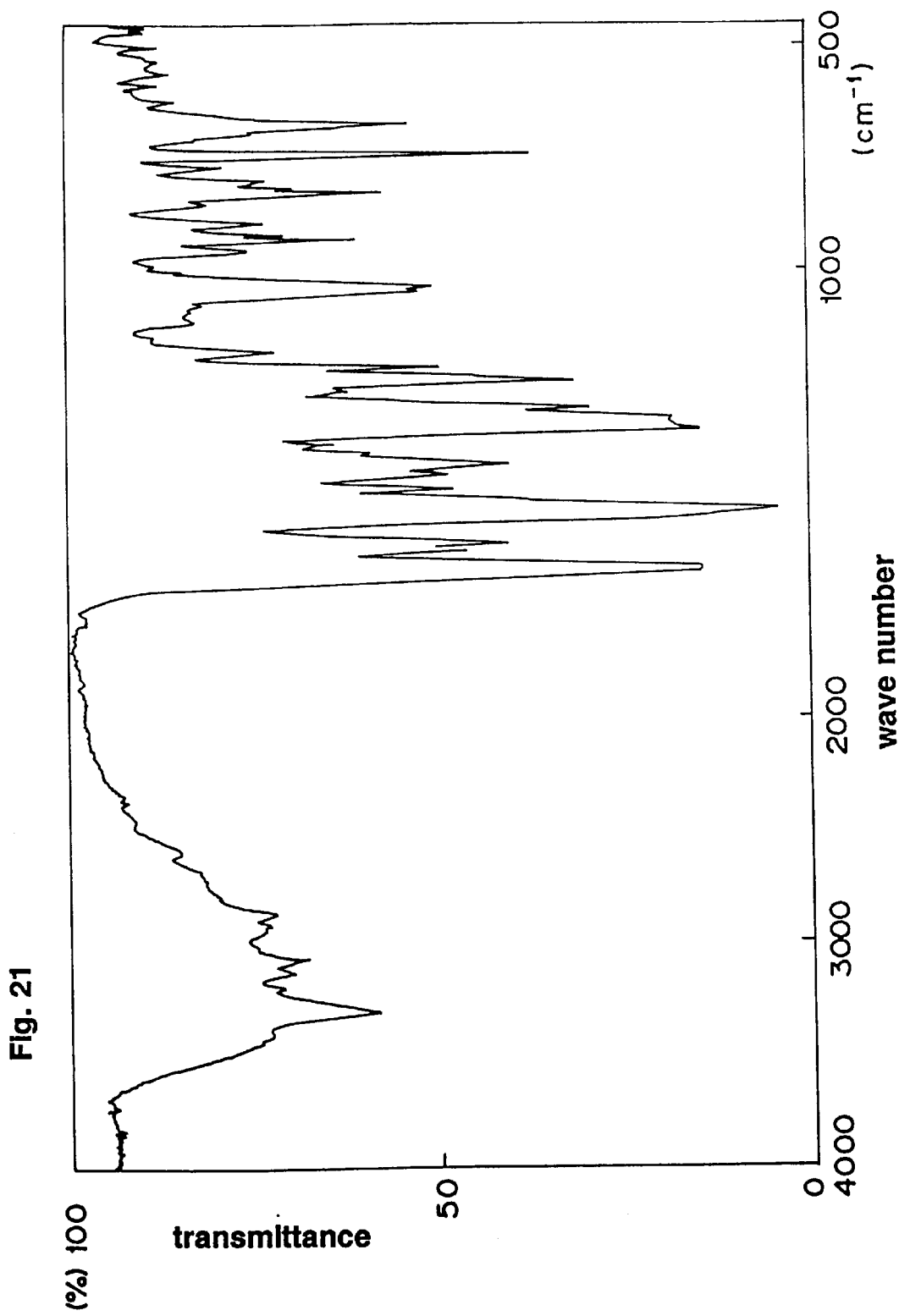
FIG. 21 is a graph illustrating an infrared absorption spectrum of the compound obtained in Example 21.

An infrared spectrum (KBr method) of this compound is shown in FIG. 21.

EXAMPLE 22

Synthesis of 1-bromo-2-hydroxy-3,6-dihydroxycarbonylnaphthalene

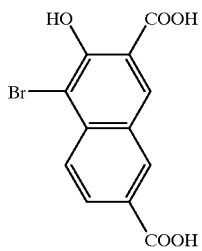

2-Hydroxy-3,6-di-hydroxycarbonylnaphthalene (11.8 g) was dissolved in chloroform (300 g) and dimethyl sulfoxide (100 g), followed by ice-cooling. Then, a solution of bromine (8.0 g) and chloroform (50 g) was added dropwise at not more than 5° C. over 2 hours. After continuously stirring for 1 hour, this solution was poured into water (1500 g) dropwise. The deposit was filtered and then washed with water and dispersed in a small amount of methanol. The dispersion was concentrated under reduced pressure at room temperature and then dried under vacuum to obtain 15.1 g of 1-bromo-2-hydroxy-3,6-di-hydroxycarbonylnaphthalene as a whitish brown crystal (DSC analysis value: 145.2° C.).

Figure 22:
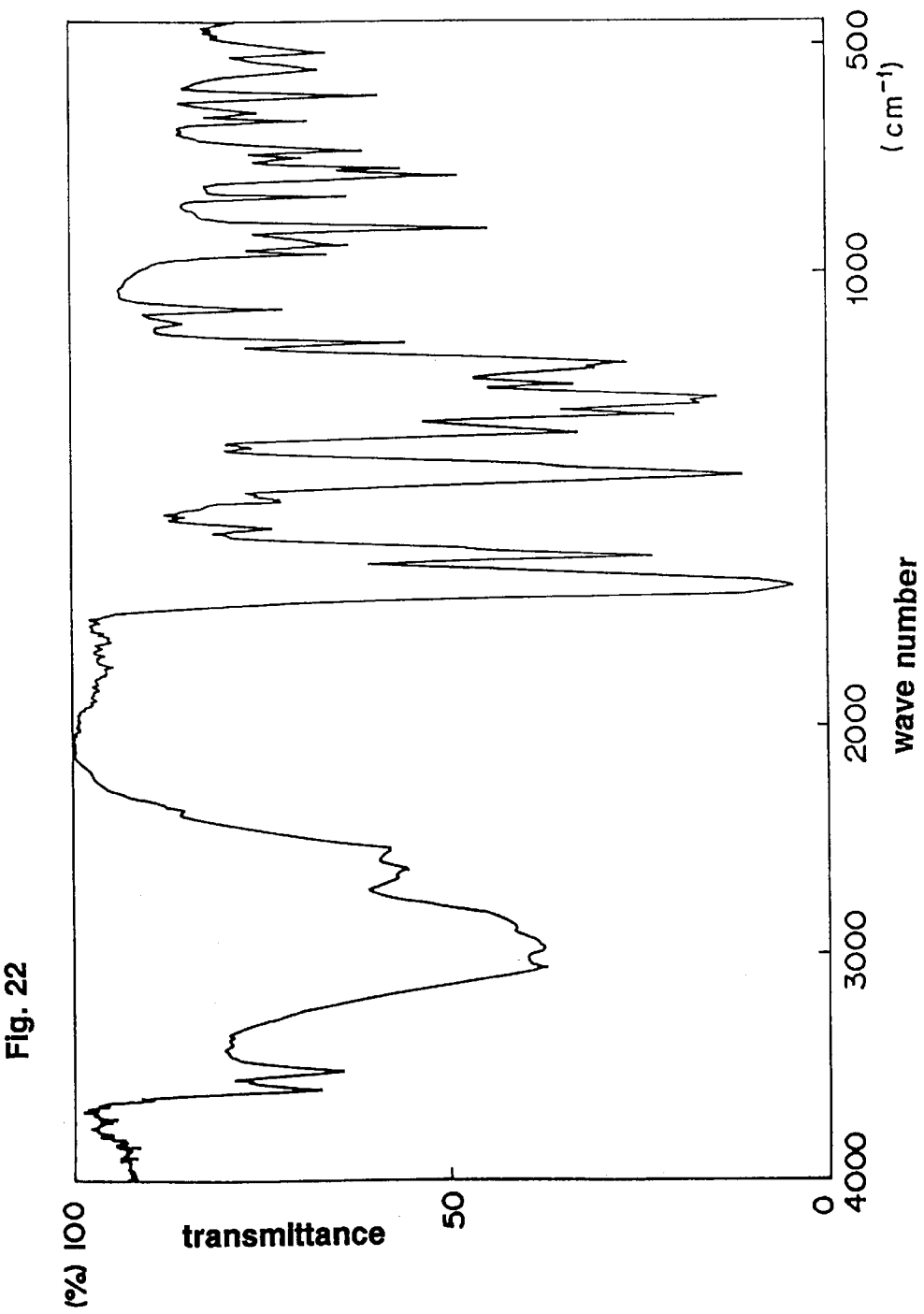
FIG. 22 is a graph illustrating an infrared absorption spectrum of the compound obtained in Example 22.

An infrared spectrum (KBr method) of this compound is shown in FIG. 22.

EXAMPLE 23

Synthesis of 1-bromo-2-hydroxy-3,6-di-chlorocarbonylnaphthalene

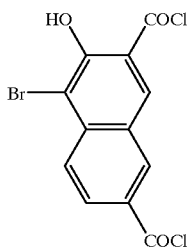

1-Bromo-2-hydroxy-3,6-di-hydroxycarbonylnaphthalene (3.2 g) obtained in Example 22 was dispersed in xylene (100 g) and N,N-dimethylformamide (0.1 g) was further added. Then, a solution of thionyl chloride (6.8 g) and xylene (30 g) was added dropwise over about 30 minutes. Then, the mixture was heated to 70° C. and reacted for 2.5 hours. The insoluble unreacted raw material was removed by filtration, and then xylene and excess thionyl chloride were distilled off under reduced pressure to obtain 3.5 g of an acid chloride (DSC analysis value: 162.0° C.).

Figure 23:
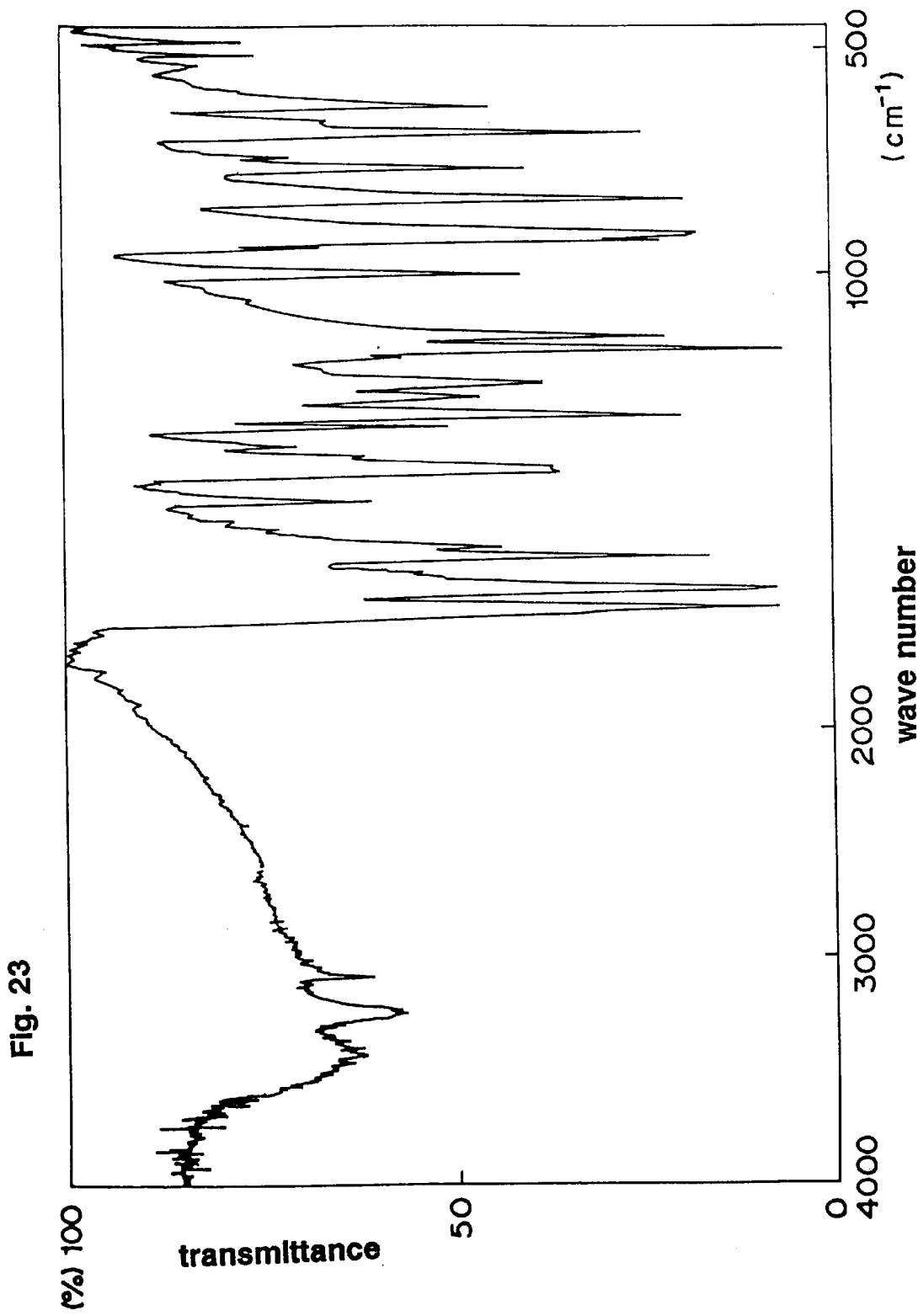
FIG. 23 is a graph illustrating an infrared absorption spectrum of the compound obtained in Example 23.

An infrared spectrum (KBr method) of this compound is shown in FIG. 23.

EXAMPLE 24

Synthesis of 2-benzyloxy-3,6-di-benzyloxycarbonylnaphthalene

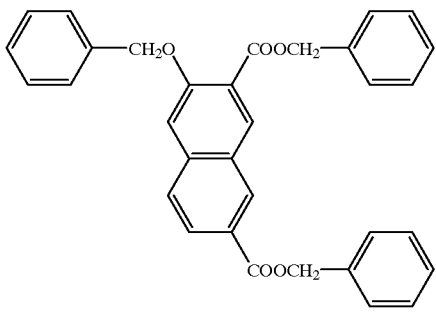

2-Hydroxy-3,6-di-hydroxycarbonylnaphthalene (2.4 g) was dissolved in dimethylformamide (50 g), followed by heating to 100° C. Potassium carbonate (4.6 g) was slowly added and benzyl chloride (4.2 g) was added dropwise. After heating for about 20 hours, the reaction solution was poured into a mixed solution of water (300 g) and methanol (100 g). The deposit was filtered and then washed with water to obtain 3.5 g of 2-benzyloxy-3,6-di-benzyloxycarbonylnaphthalene as whitish yellow powder (DSC analysis value: 100.5° C.).

Figure 24:
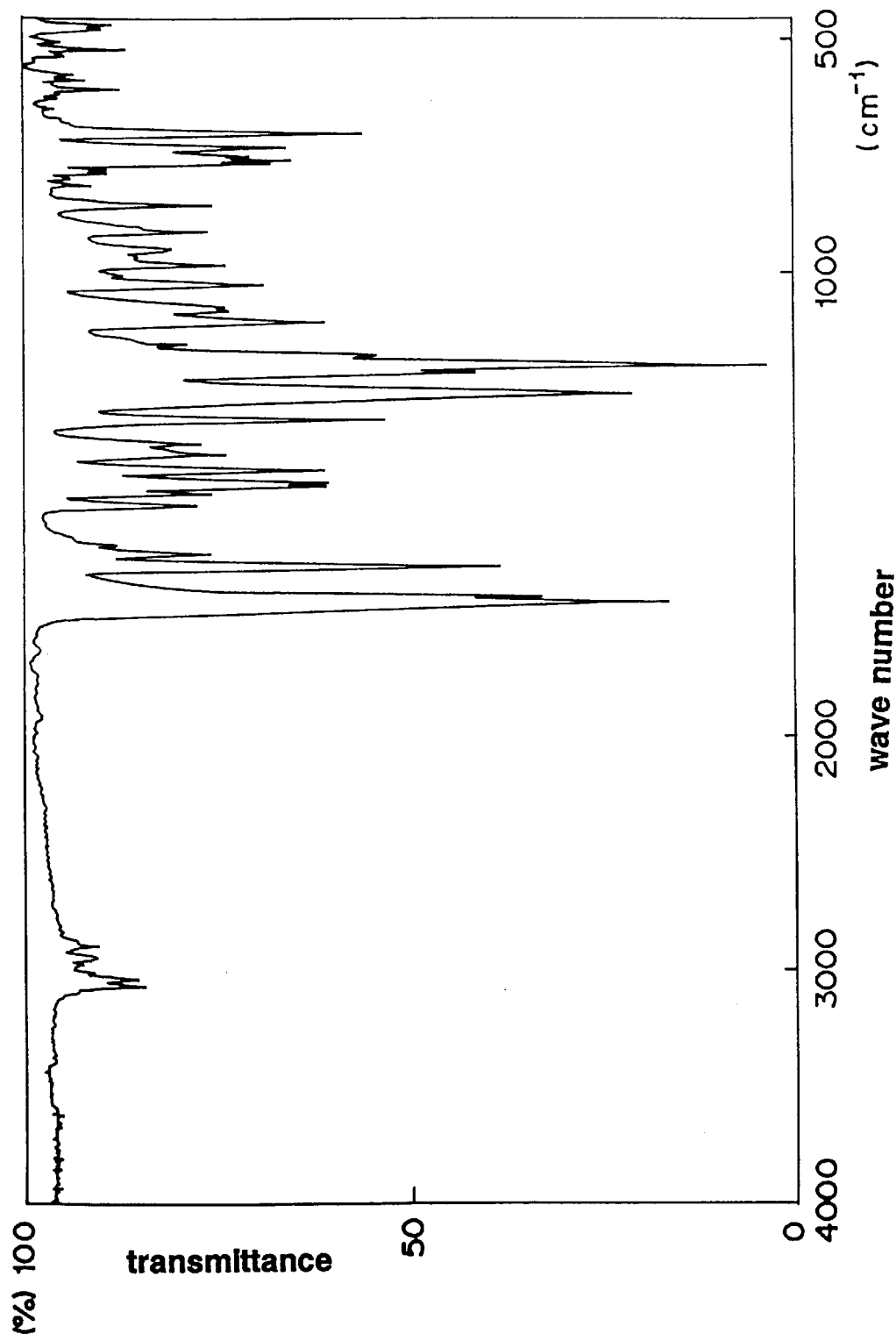
FIG. 24 is a graph illustrating an infrared absorption spectrum of the compound obtained in Example 24.

An infrared spectrum (KBr method) of this compound is shown in FIG. 24.

EXAMPLE 25

Synthesis of 1-nitroso-2-hydroxy-3,6-bis(2,4-dimethylphenylaminocarbonyl naphthalene

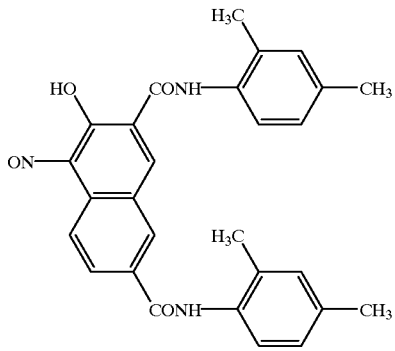

2-Hydroxy-3,6-bis(2,4-dimethylphenylaminocarbonyl) naphthalene (1.5 g) obtained in Example 3 was dissolved in acetic acid (7.0 g), ethanol (7.0 g) and N-methyl-2-pyrrolidone (18.0 g), followed by cooling to 0° C. A solution prepared by dissolving sodium nitrite (0.97 g) in water (4.2 g) was added dropwise at 0 to 1° C. and then the mixture was reacted at the same temperature for 2 hours. After stirring at room temperature overnight, the deposited crystal was filtered, washed with a small amount of ethanol and dried under vacuum at 50° C. to obtain 1.4 g of a colored crystal. This crystal (1.4 g) was dissolved in N-methyl-2-pyrrolidone (58.3 g) with heating, treated with active carbon (0.09 g) and then subjected to thermal filtration. The filtrate was diluted with methanol to deposit a crystal, which was filtered, washed with methanol and then dried to obtain 0.58 g of pale brown 1-nitroso-2-hydroxy-3,6-bis(2,4-dimethylaminocarbonyl)naphthalene (DSC analysis value: 267.3° C.).

Figure 25:
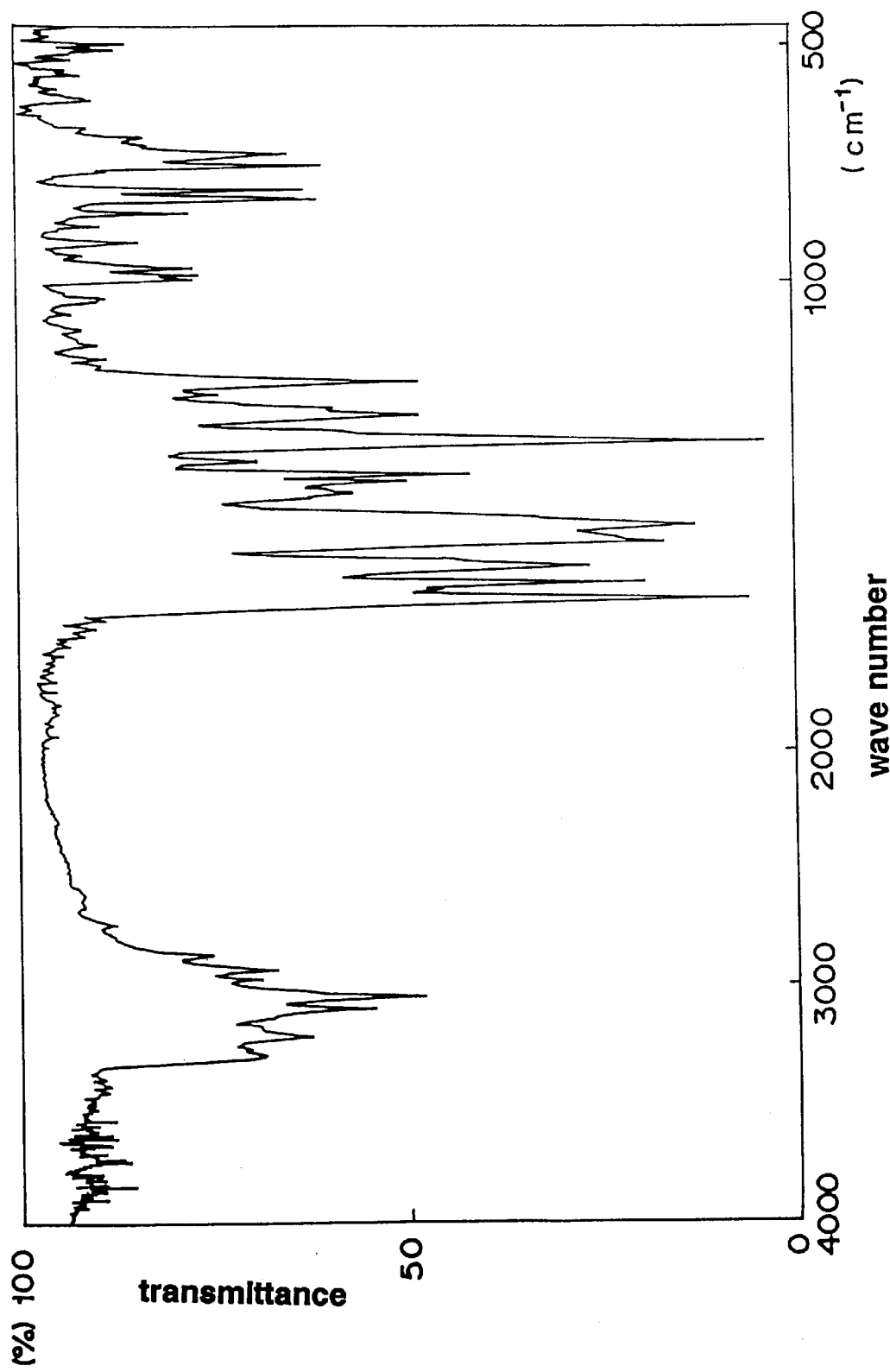
FIG. 25 is a graph illustrating an infrared absorption spectrum of the compound obtained in Example 25.

An infrared spectrum (KBr method) of this compound is shown in FIG. 25.

EXAMPLE 26

Synthesis of 2-hydroxy-3,6-dimethoxycarbonylnaphthalene

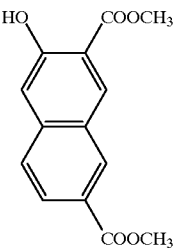

2-Hydroxy-3,6-dichlorocarbonylnaphthalene (12.0 g) obtained in Example 6 was mixed with methanol (600 g) and, after refluxing for 2 hours, active carbon (1.0 g) was added and the mixture was subjected to thermal filtration. The filtrate was cooled to deposit a crystal, which was filtered and then dried to obtain 8.3 g of a crude crystal. The crude crystal was purified with methanol (300 g) to obtain 4.0 g of 2-hydroxy-3,6-dimethoxycarbonylnaphthalene as a pale yellow crystal (DSC analysis value: 163.1° C.).

Figure 26:
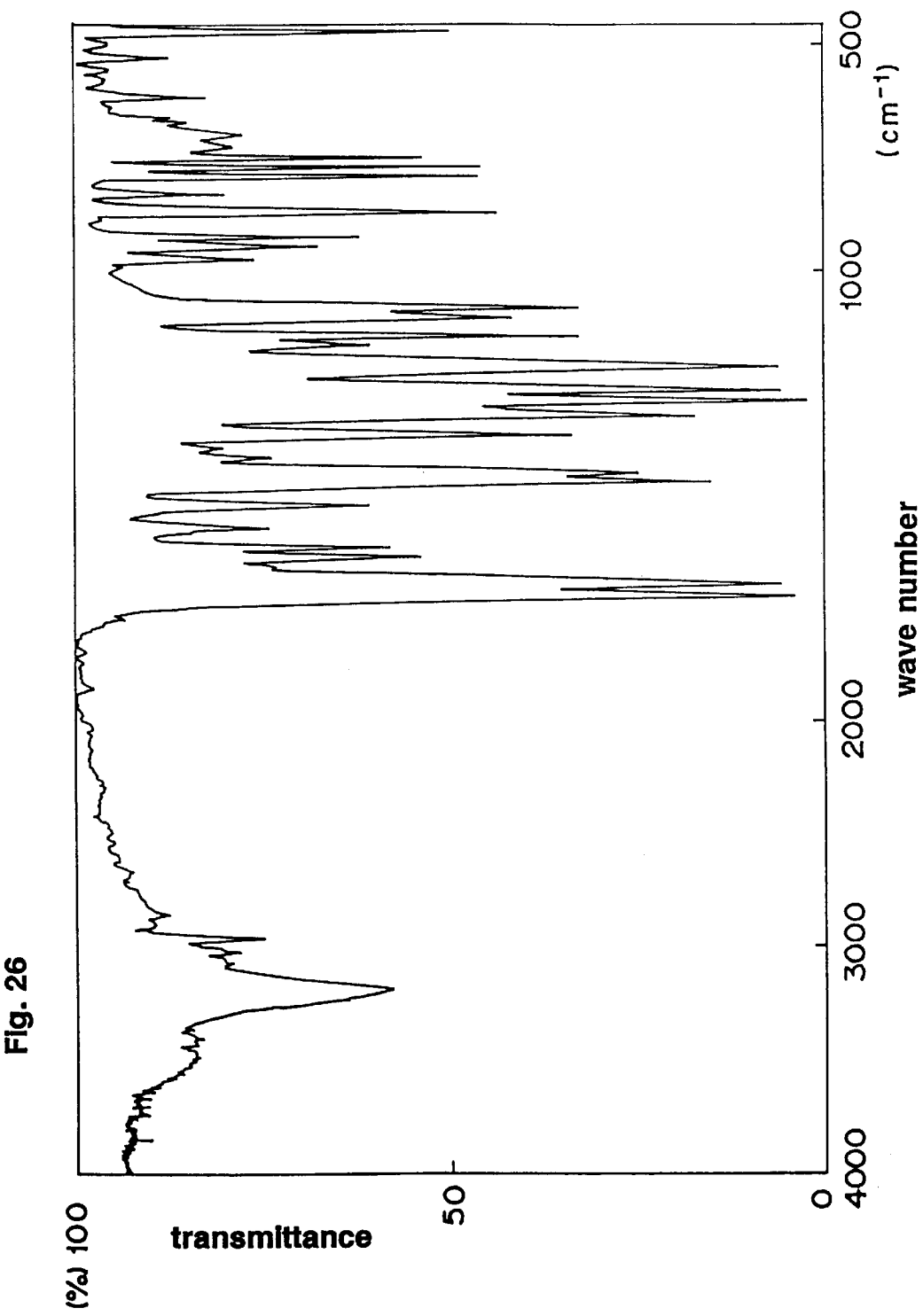
FIG. 26 is a graph illustrating an infrared absorption spectrum of the compound obtained in Example 26.

An infrared spectrum (KBr method) of this compound is shown in FIG. 26.

EXAMPLE 27

Synthesis of 2-hydroxy-3-hydroxycarbonyl-6-methoxycarbonylnaphthalene

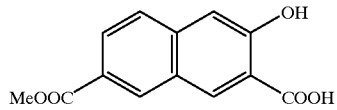

2-Hydroxy-3,6-di-hydroxycarbonylnaphthalene (11.6 g) was dispersed in anhydrous acetonitrile (116.0 g) and N-methyl-2-pyrrolidone (39.0 g). Then, methyl iodide (7.85 g) was added and 1.8-diazabicyclo[5.4.0]undec-7-ene (hereinafter referred to as "DBU") (8.37 g) was added dropwise over 5 minutes, followed by heating at 50° C. overnight. Further methyl iodide (2.32 g) and DBU (2.42 g) was added and mixture was stirred overnight. The deposited crystal was filtered and then dried under reduced pressure to obtain 7.29 g of a crude crystal of 2-hydroxy-3-hydroxycarbonyl-6-methoxycarbonylnaphthalene. Aliquot of this crystal (1.52 g) was dissolved in ethyl acetate (30.2 g) and an aqueous 5% sodium hydrogencarbonate. The solution was separated into the organic layer and the aqueous layer, and then the organic layer was extracted with an aqueous 5% sodium hydrogencarbonate solution (10.3 g) and aqueous extract was combined with the above aqueous layer. To this aqueous layer was added dropwise 10% hydrochloric acid until the pH becomes 7 while ice-cooling. The deposited crystal was filtered and then dried under reduced pressure to obtain 1.02 g of 2-hydroxy-3-hydroxycarbonyl-6-methoxycarbonylnaphthalene (DSC analysis value: 295.1° C.).

Figure 27:
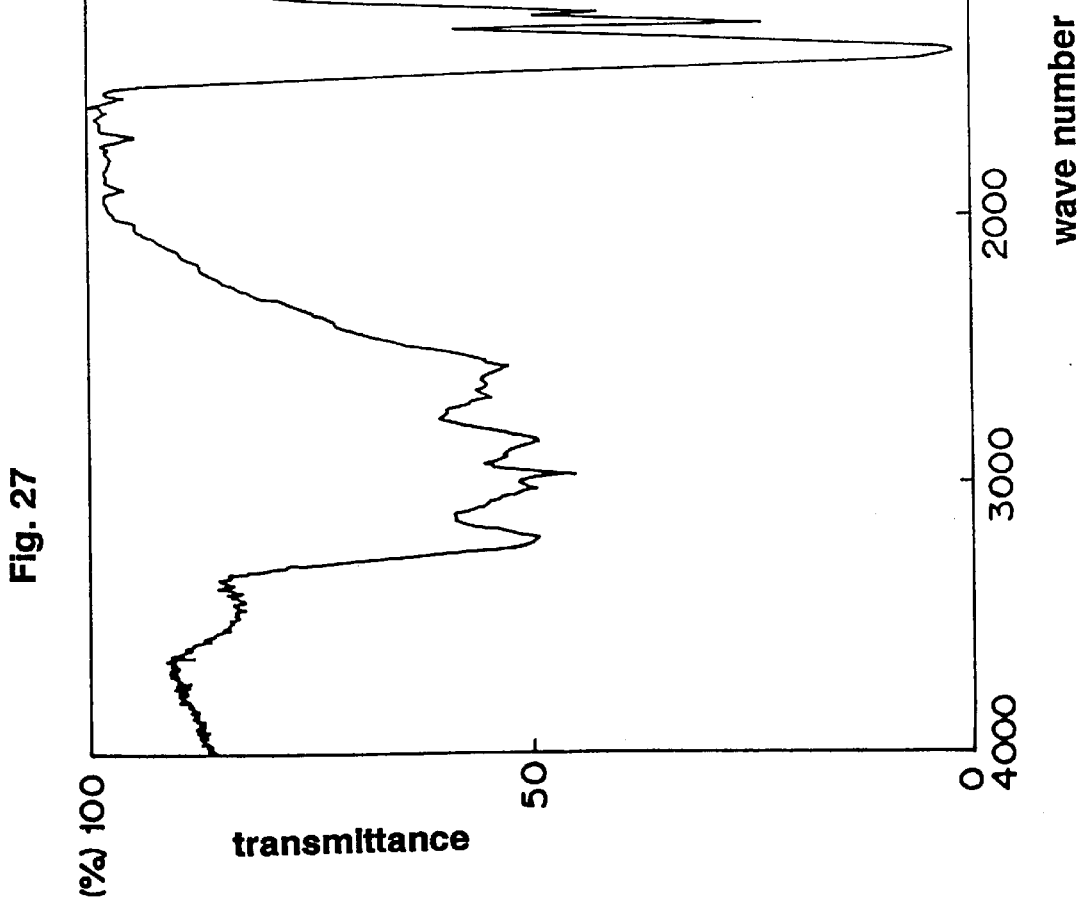
FIG. 27 is a graph illustrating an infrared absorption spectrum of the compound obtained in Example 27.

An infrared spectrum (KBr method) of this compound is shown in FIG. 27.

EXAMPLE 28

Synthesis of 2-hydroxy-3-phenylaminocarbonyl-6-methoxycarbonylnaphthalene

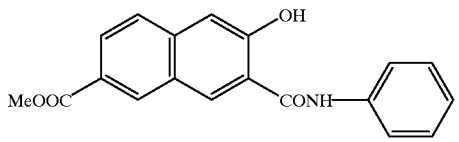

2-Hydroxy-3-hydroxycarbonyl-6-methoxycarbonynaphthalene (0.50 g) obtained in Example 27 was suspended in N-methyl-2-pyrrolidone (5.00 g) and dicyclohexylcarbodiimide (hereinafter referred to as "DCC") (0.42 g) and aniline (0.57 g) were added, followed by stirring at room temperature overnight. After heating to 50° C., DCC (0.18 g) was further added and the mixture was stirred overnight. The reaction solution was concentrated under reduced pressure and the residue was purified twice by subjecting to silica gel chromatography to obtain 0.65 g of 2-hydroxy-3-phenylaminocarbonyl-6-methoxycarbonylnaphthalene (DSC analysis value: 238.1° C.).

Figure 28:
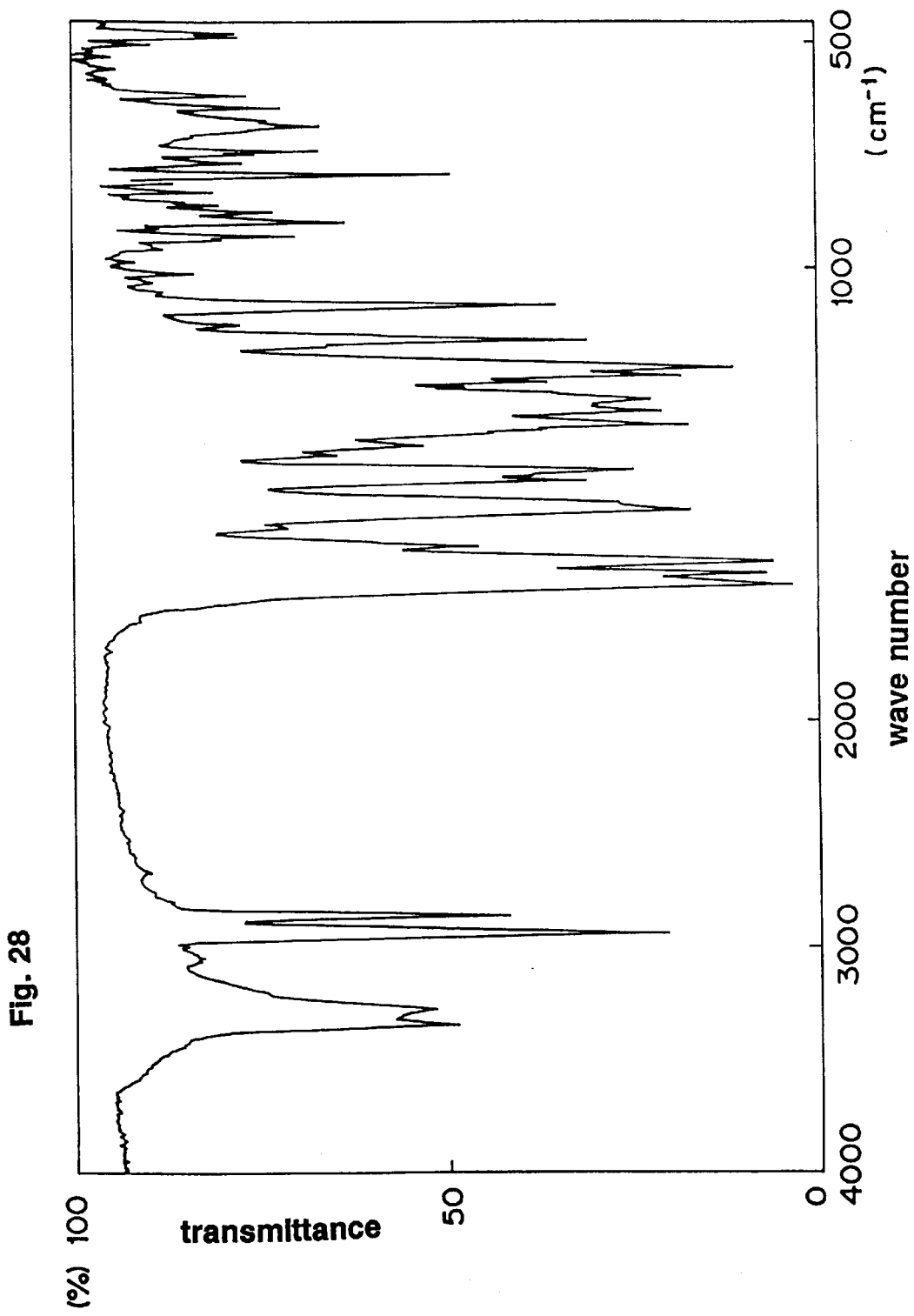
FIG. 28 is a graph illustrating an infrared absorption spectrum of the compound obtained in Example 28.

An infrared spectrum (KBr method) of this compound is shown in FIG. 28.

EXAMPLE 29

Synthesis of sodium 3-phenylaminocarbonyl-6-methoxycarbonyl-2-naphthoate

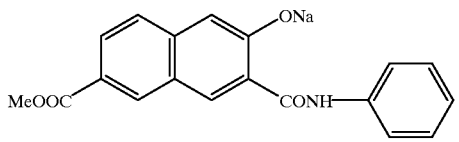

2-Hydroxy-3-phenylaminocarbonyl-6-methoxycarbonylnaphthalene (0.45 g) obtained in Example 28 was suspended in methanol (10.0 g) and 1N-sodium hydroxide (2.8 g) was added under ice-cooling. A yellow crystal of sodium 3-phenylaminocarbonyl-6-methoxycarbonyl-2-naphthoate, which was once dissolved and deposited, was filtered and then dried under reduced pressure to obtain 0.32 g of it.

Figure 29:
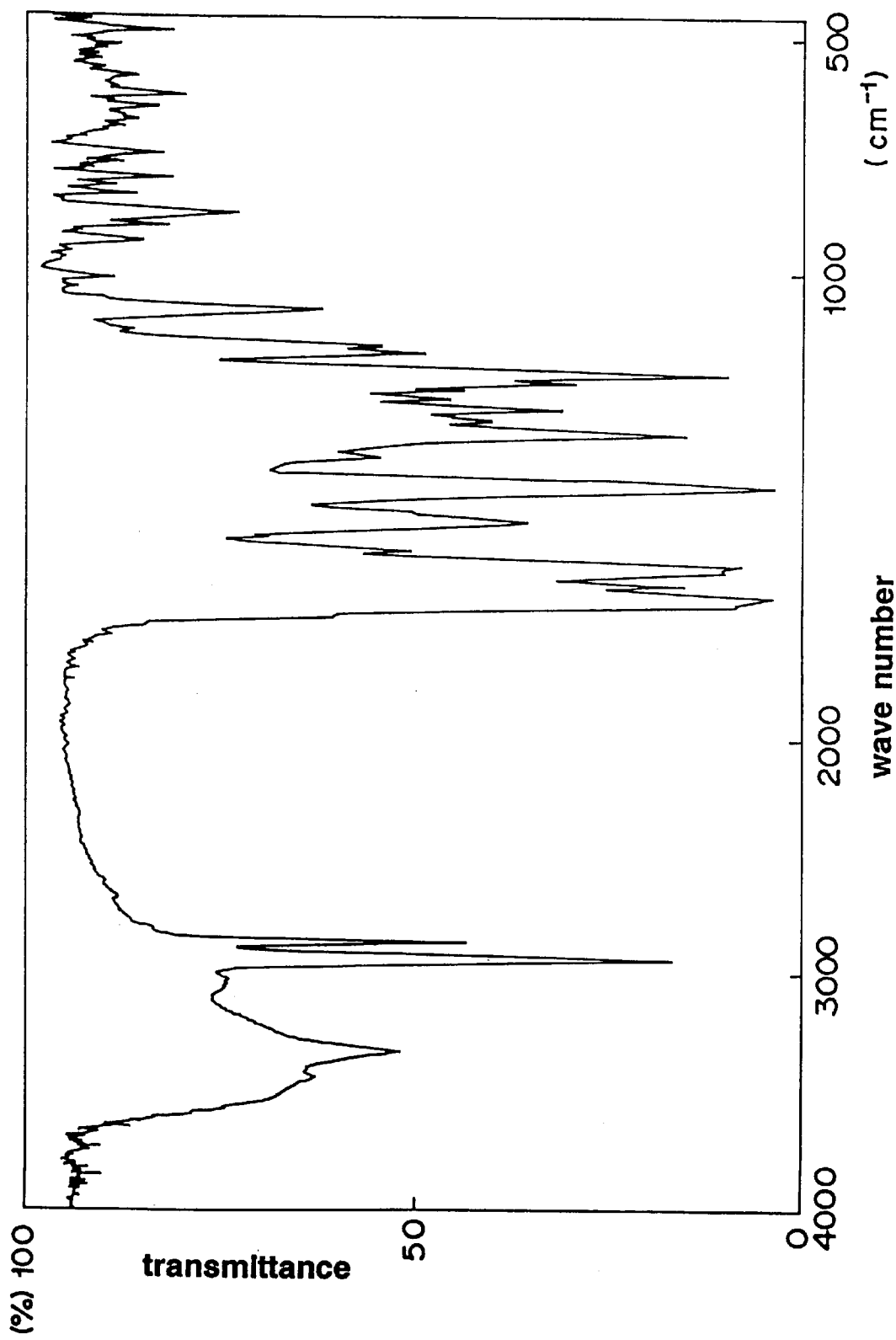
FIG. 29 is a graph illustrating an infrared absorption spectrum of the compound obtained in Example 29.

An infrared spectrum (KBr method) of this compound is shown in FIG. 29.

EXAMPLE 30

Synthesis of 2-hydroxy-3-phenylaminocarbonyl-6-hydroxycarbonylnaphthalene

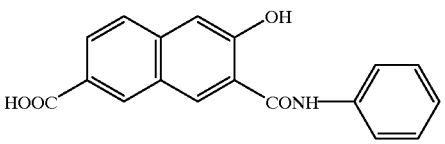

Sodium 3-phenylaminocarbonyl-6-methoxycarbonyl-2-naphthoate (0.081 g) obtained in Example 29 was suspended in methanol (8.10 g) and deionized water (8.13 g) and 1N-sodium hydroxide (4.0 g) was added dropwise under ice-cooling, followed by stirring overnight. The reaction solution was freeze-dried and the resultant solid was dissolved in water. The solution was acidified with diluted hydrochloric acid and the deposited crystal was filtered. The crystal was dried under reduced pressure to obtain 0.057 g of 2-hydroxy-3-phenylaminocarbonyl-6-hydroxycarbonylnaphthalene.

Figure 30:
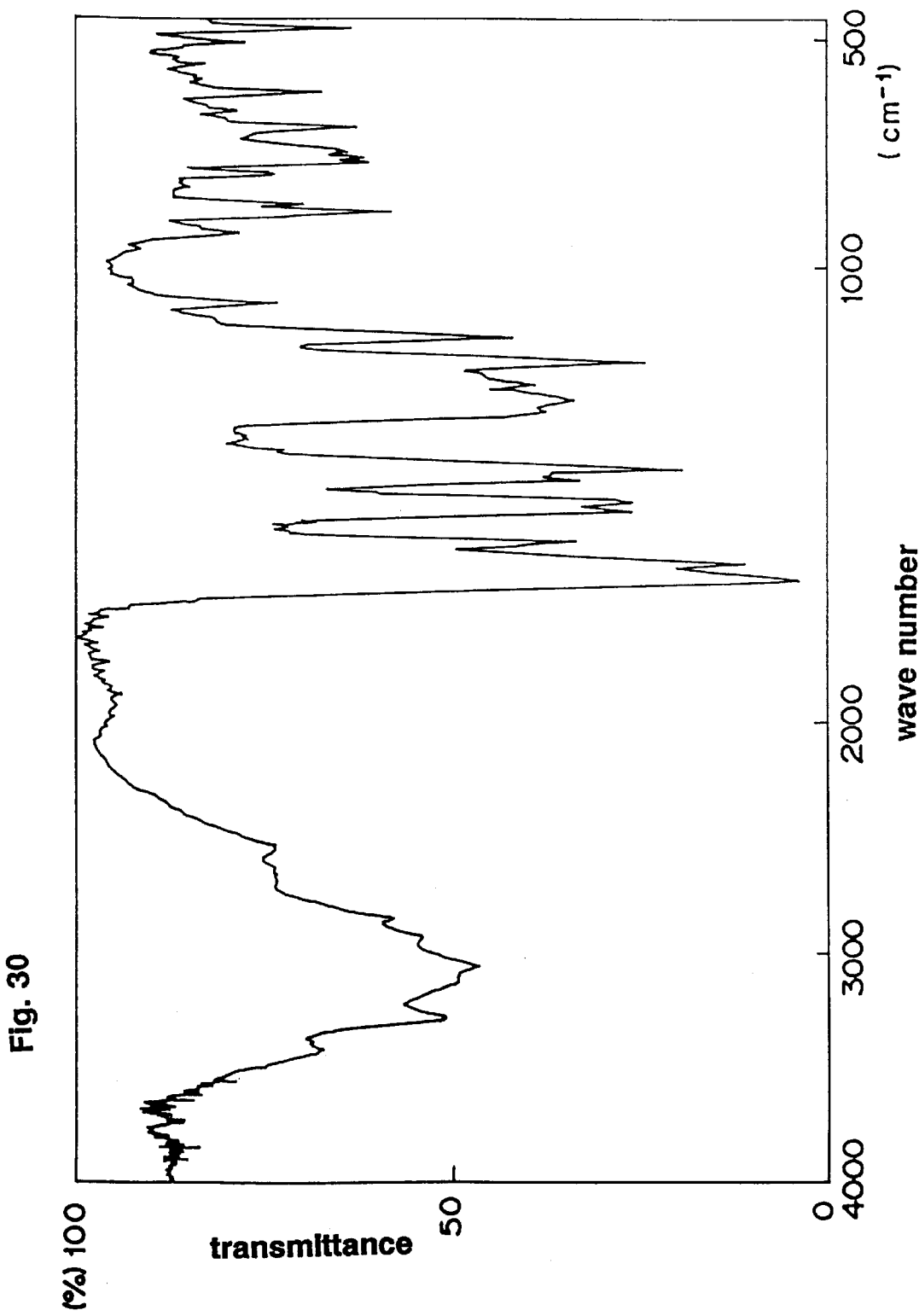
FIG. 30 is a graph illustrating an infrared absorption spectrum of the compound obtained in Example 30.

An infrared spectrum (KBr method) of this compound is shown in FIG. 30.

EXAMPLE 31

Synthesis of 2-hydroxy-3-phenacyloxycarbonyl-6-methoxycarbonylnaphthalene

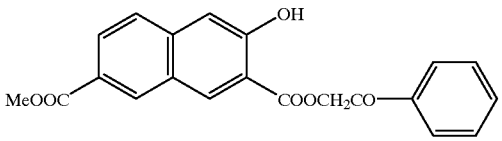

To anhydrous N,N-dimethylformamide (hereinafter referred to as "DMF") (10.0 g) were added potassium fluoride (0.209 g) and phenacyl bromide (0.647 g), followed by stirring on an oil bath at 25° C. for about 1 minute. 2-Hydroxy-3-hydroxycarbonyl-6-methoxycarbonylnaphthalene (0.80 g) was dissolved in anhydrous DMF (5.20 g) and the resulting solution was added to the reaction solution. After the completion of the reaction, ethyl acetate, diethyl ether and aqueous 5% sodium hydrogencarbonate were added. Then, an insoluble matter was removed by filtration and the residue was partitioned. The organic layer was washed with a saturated sodium chloride aqueous solution and then dried over anhydrous magnesium sulfate. After the desiccant was removed by filtration, the filtrate was concentrated under reduced pressure. The resultant residue was purified by subjecting to silica gel chromatography to obtain 0.57 g of 2-hydroxy-3-phenacyloxycarbonyl-6-methoxycarbonylnaphthalene (DSC analysis value: 177.7° C.).

Figure 31:
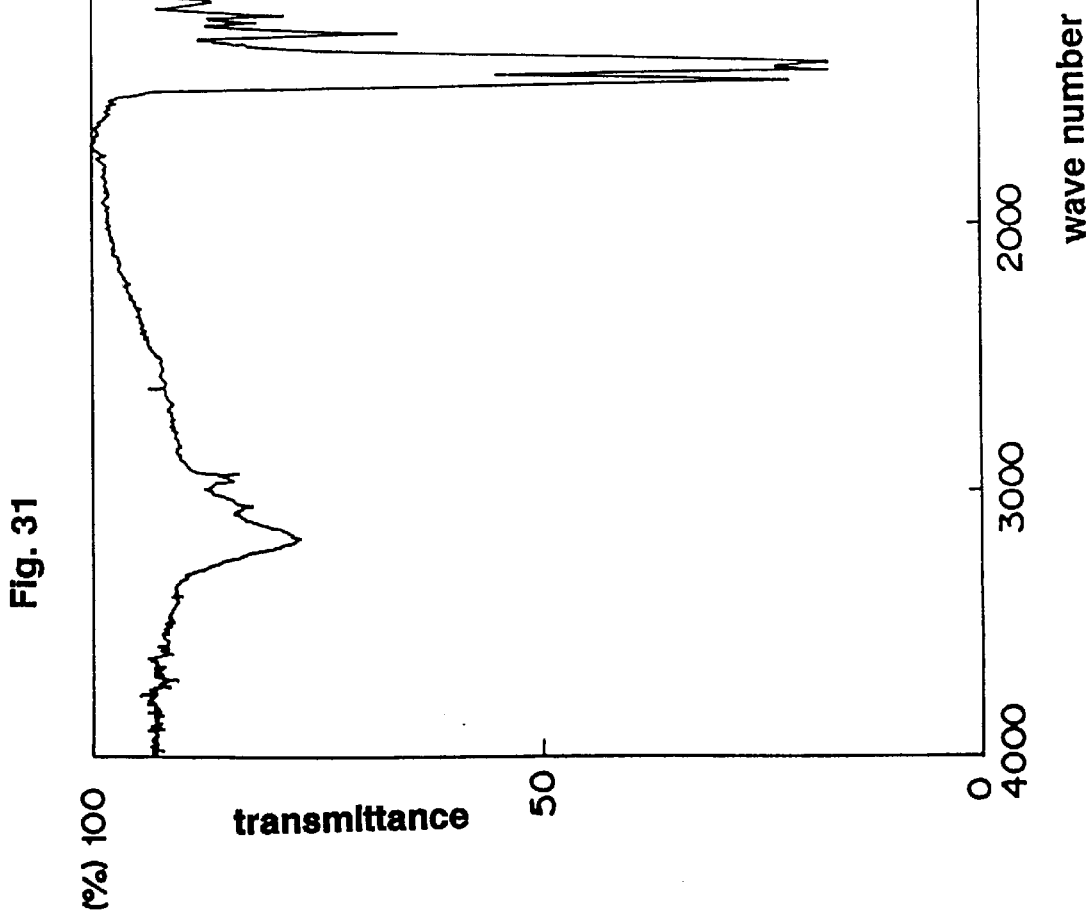
FIG. 31 is a graph illustrating an infrared absorption spectrum of the compound obtained in Example 31.

An infrared spectrum (KBr method) of this compound is shown in FIG. 31.

EXAMPLE 32

Synthesis of 2-benzyloxy-3,6-di-methoxycarbonylnaphthalene

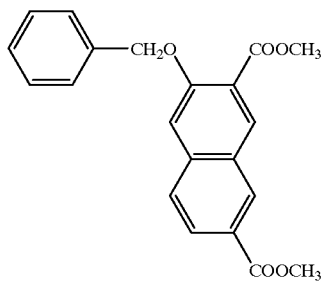

2-Hydroxy-3,6-di-methoxycarbonylnaphthalene (2.7 g) obtained in Example 26 was dissolved in N,N-dimethylformamide (50 g), followed by heating to 100° C. Potassium carbonate (1.5 g) was slowly added and benzyl chloride (1.4 g) was added dropwise. After heating for about 20 hours, the reaction solution was poured into a mixed solution of water (300 g) and methanol (100 g). The deposit was filtered and then washed with water to obtain 2.5 g of 2-benzyloxy-3,6-di-methoxycarbonylnaphthalene as whitish yellow powder (DSC analysis value: 113.8° C.).

Figure 32:
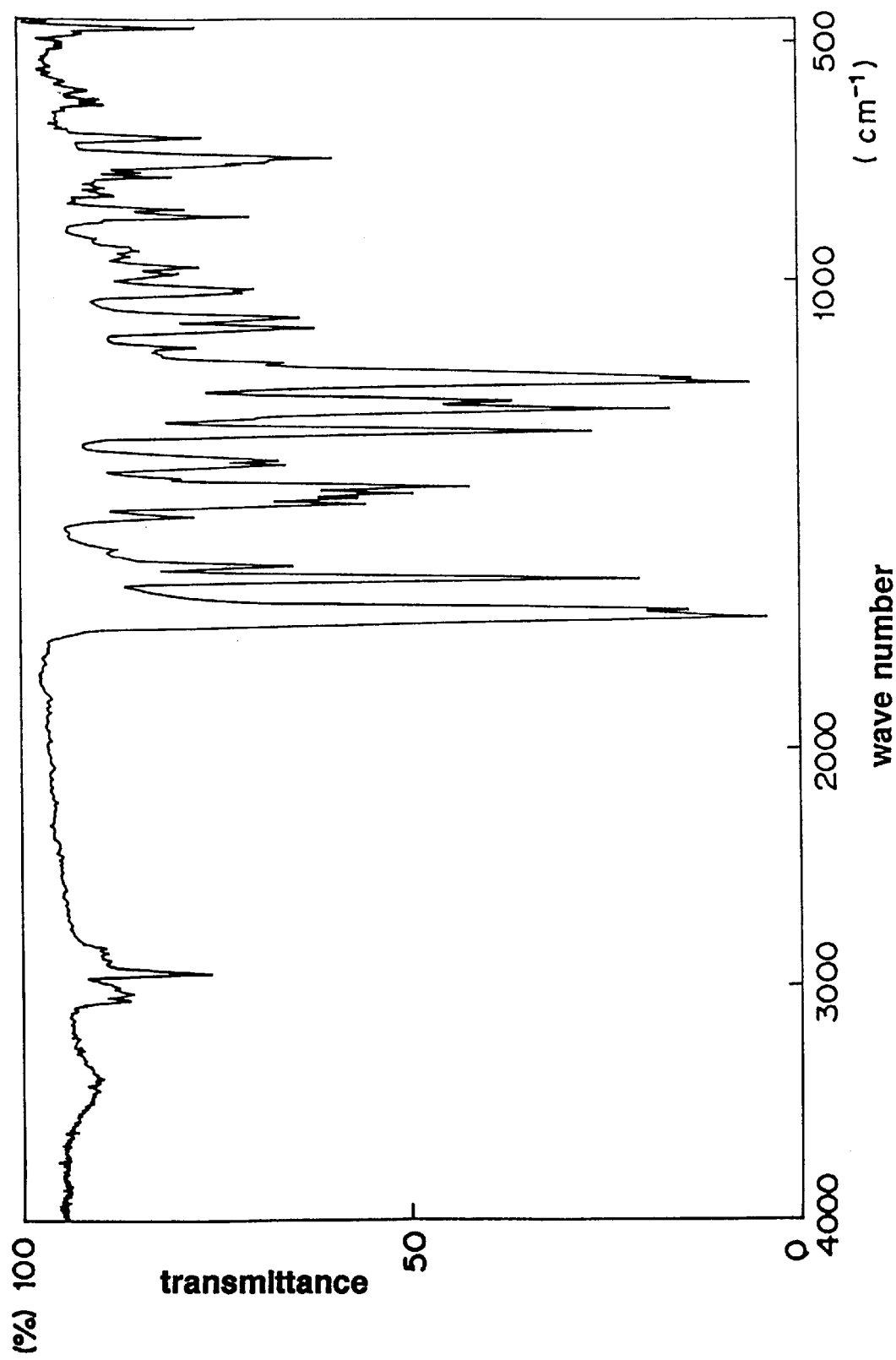
FIG. 32 is a graph illustrating an infrared absorption spectrum of the compound obtained in Example 32.

An infrared spectrum (KBr method) of this compound is shown in FIG. 32.

EXAMPLE 33

Synthesis of 2-benzyloxy-3,6-di-hydroxycarbonylnaphthalene

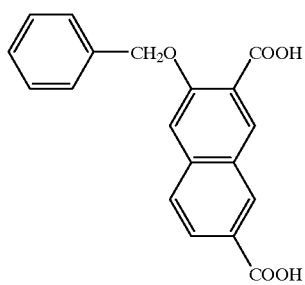

2-Benzyloxy-3,6-di-methoxycarbonylnaphthalene (0.52 g) obtained in Example 32 was dissolved in N-methyl-2-pyrrodidone (10 g) and methanol (10 g) and water (20 g) were added. Furthermore, an aqueous 1N-sodium hydroxide (4.5 g) was added, followed by stirring at about 60° C. for 2 hours. After the insoluble formed during the reaction was removed by filtration, the solution was adjusted to about pH 4 using aqueous 10% hydrochloric acid. The deposit was filtered and then washed with water to obtain 0.41 g of 2-benzyloxy-3,6-di-hydroxycarbonylnaphthalene as pale brown powder (DSC analysis value: 241.3° C.).

Figure 33:
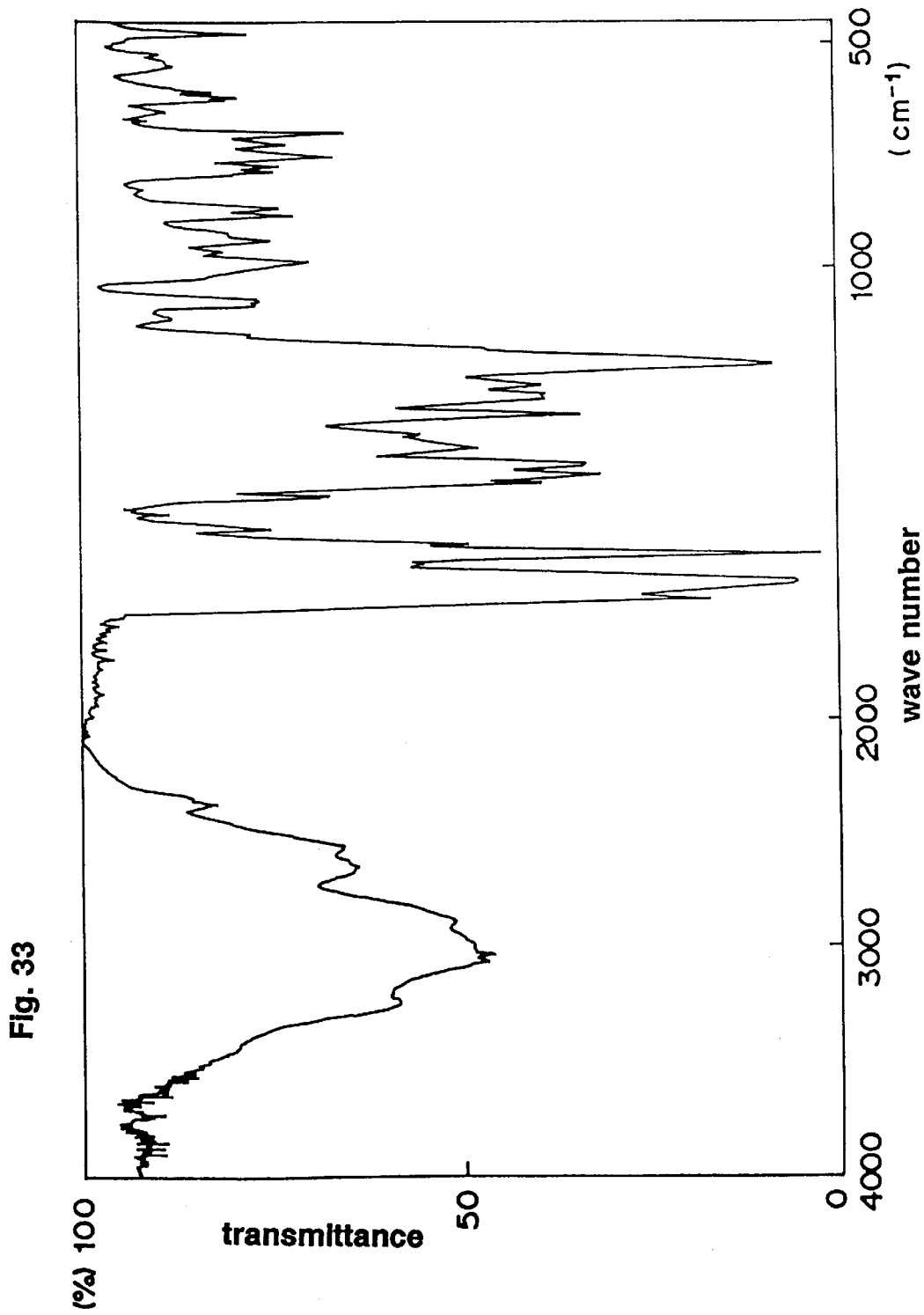
FIG. 33 is a graph illustrating an infrared absorption spectrum of the compound obtained in Example 33.

An infrared spectrum (KBr method) of this compound is shown in FIG. 33.

EXAMPLE 34

Synthesis of 2-acetoxy-3,6-di-methoxycarbonylnaphthalene

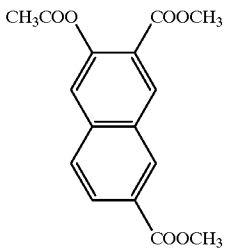

2-Hydroxy-3,6-di-methoxycarbonylnaphthalene (2.6 g) obtained in Example 26 was suspended in acetic anhydride (10.0 g), acetic acid (12.0 g) and N,N-dimethylformamide (20.0 g) and 4-dimethylaminopyridine (0.1 g) was added, followed by heating to 50° C. After heating for about 6 hours, the reaction solution was poured into a mixed solution of water (300 g) and methanol (100 g). The deposit was filtered and then washed with water to obtain 2.55 g of 2-acetoxy-3,6-di-methoxycarbonylnaphthalene as pale yellow powder (DSC analysis value: 130.6° C.).

Figure 34:
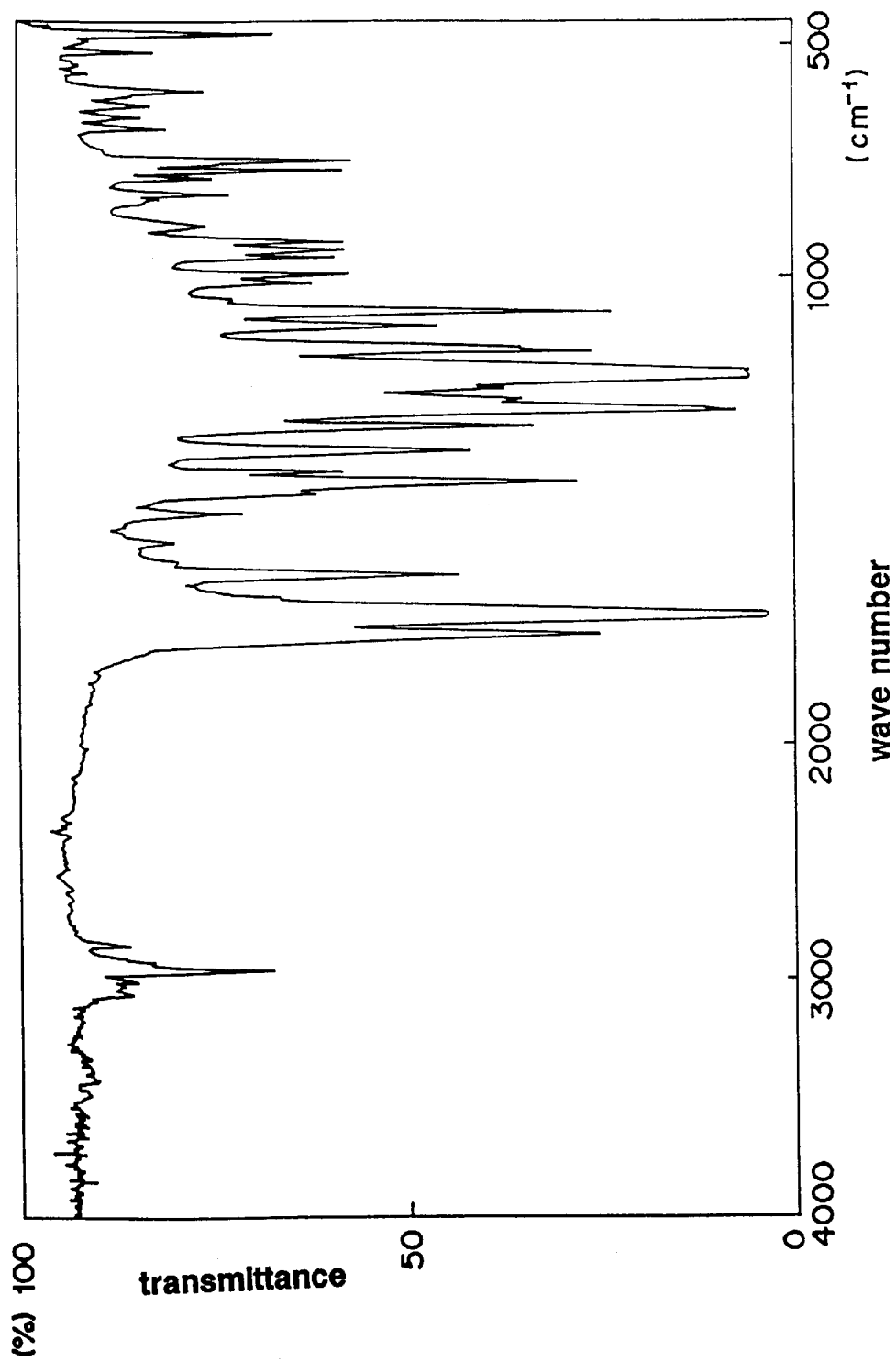
FIG. 34 is a graph illustrating an infrared absorption spectrum of the compound obtained in Example 34.

An infrared spectrum (KBr method) of this compound is shown in FIG. 34.

EXAMPLE 35

Synthesis of 2-acetoxy-3,6-di-hydroxylcarbonylnaphthalene

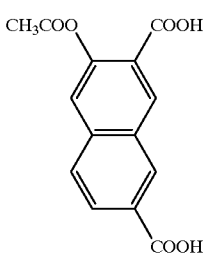

2-Hydroxy-3,6-di-hydroxycarbonylnaphthalene (12.1 g) was suspended in acetic anhydride (39.0 g), acetic acid (60.1 g) and N,N-dimethylformamide (40.0 g) and 4-dimethylaminopyridine (0.2 g) was added, followed by heating to 50° C. After heating for about 20 hours, the reaction solution was poured into a mixed solution of water (400 g) and methanol (100 g). The deposit was filtered and then washed with water to obtain 11.6 g of 2-acetoxy-3,6-di-hydroxycarbonylnaphthalene as grayish white powder (DSC analysis value: 239.2° C.).

Figure 35:
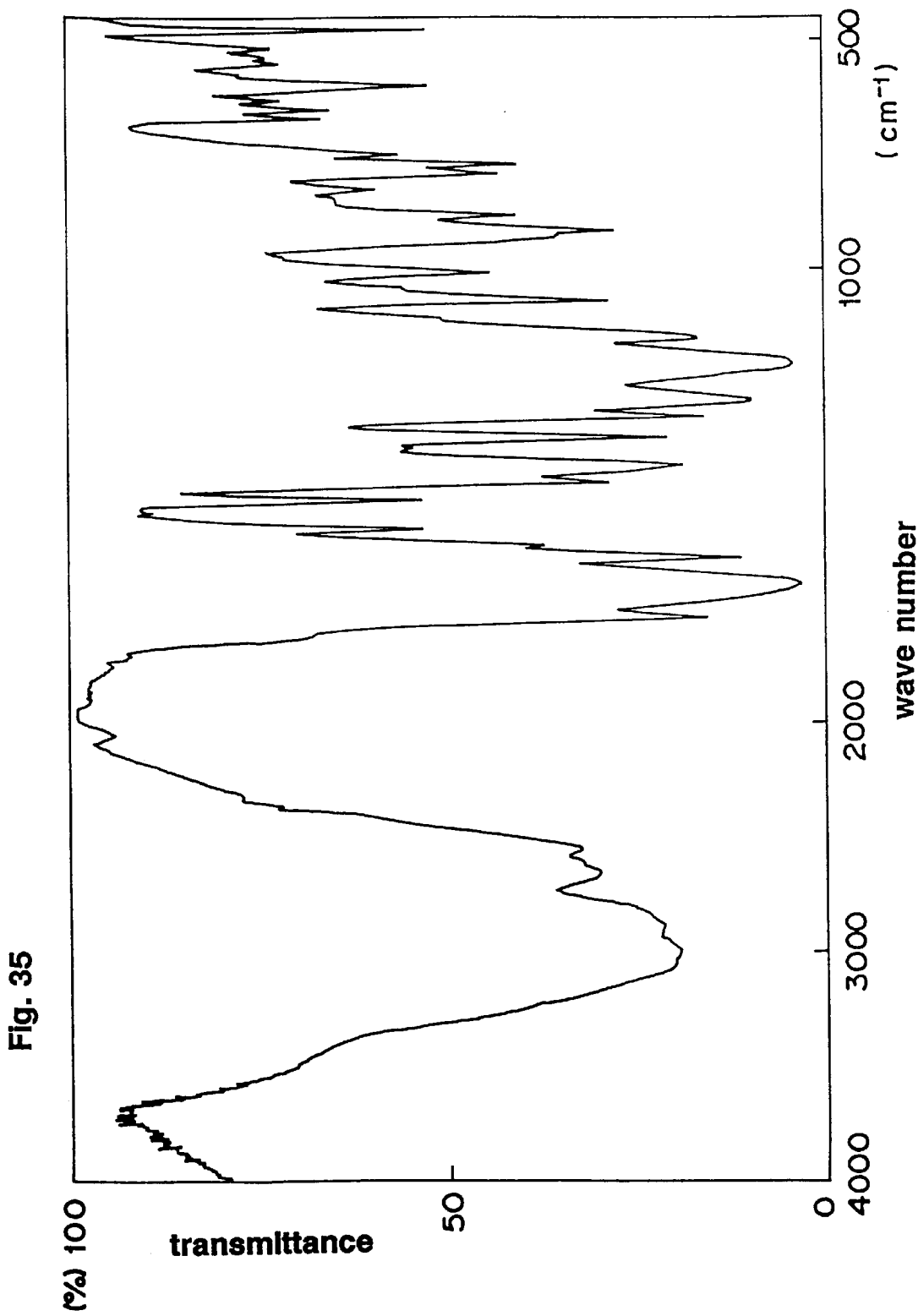
FIG. 35 is a graph illustrating an infrared absorption spectrum of the compound obtained in Example 35.

An infrared spectrum (KBr method) of this compound is shown in FIG. 35.

EXAMPLE 36

Synthesis of 2-hydroxy-3,6-di-isopropyloxycarbonylnaphthalene

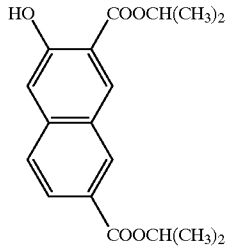

2-Hydroxy-3,6-di-dichlorocarbonylnaphthalene (1.17 g) obtained in Example 6 was mixed with isopropyl alcohol (30 g), and then the mixture was heated to 80° C. and maintained at the same temperature for about 30 minutes. After the insoluble matter was removed by filtration, the filtrate was concentrated under reduced pressure and the residue was recrystallized by using methanol to obtain 1.36 g of 2-hydroxy-3,6-di-isopropyloxycarbonylnaphthalene as pale yellow powder (DSC analysis value: 83.7° C.).

Figure 36:
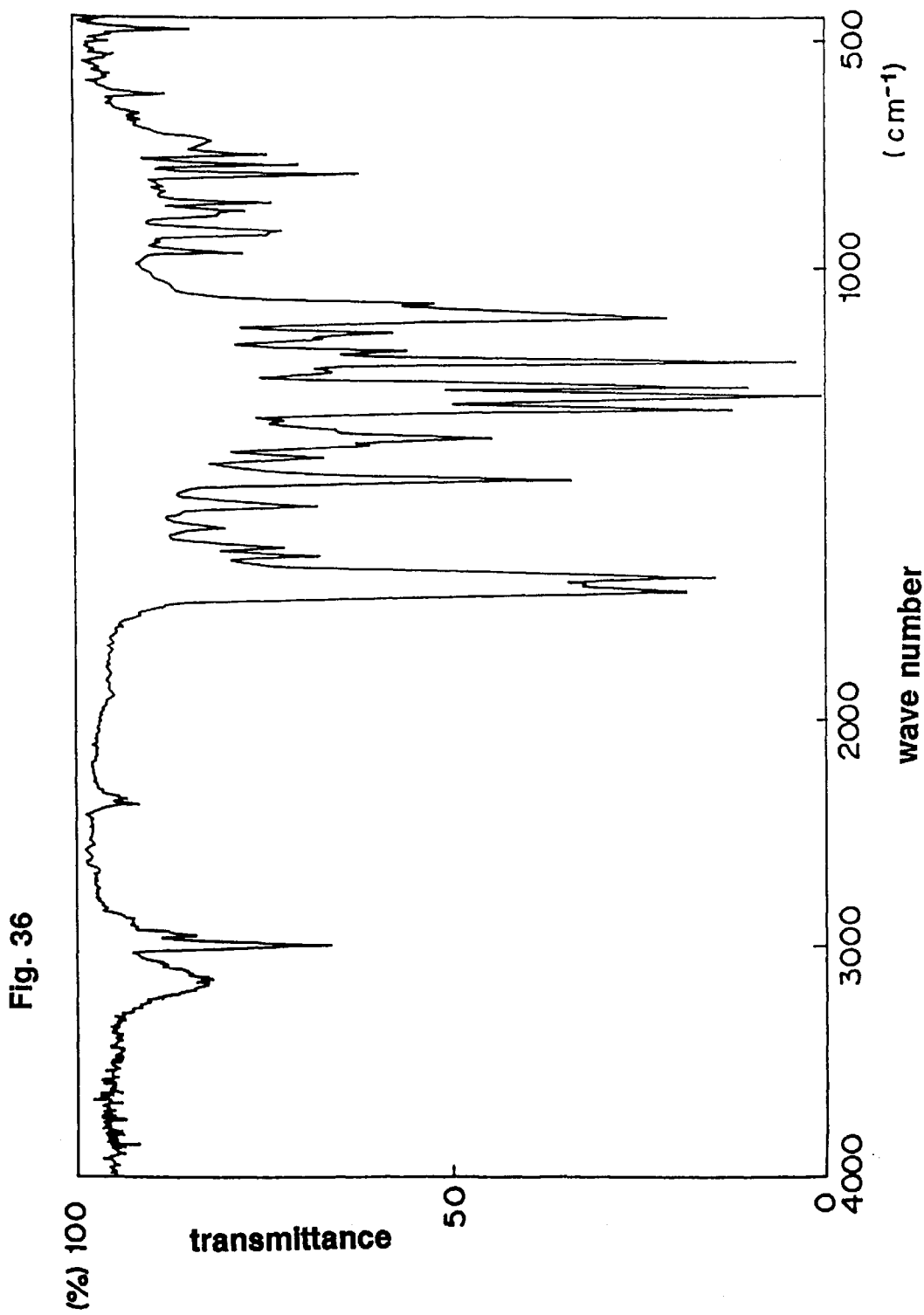
FIG. 36 is a graph illustrating an infrared absorption spectrum of the compound obtained in Example 36.

An infrared spectrum (KBr method) of this compound is shown in FIG. 36.

What is claimed is:

1. Naphthol derivatives represented by the general formula (I):

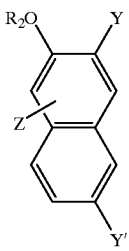

(I)

wherein
one of Y and Y' is —(CONH)$_n$—X or —COR;
the other of Y and Y' is —(CONH)$_n$—X';
X and X' may be the same or different and indicate a phenyl group, a naphthyl group, an anthraquinonyl group, a benzimidazolonyl group or a carbozolyl group, and each group may be optionally substituted;
R is a hydroxyl group, an optionally branched alkoxy group having 1 to 6 carbon atoms, a halogen atom, a benzyloxy group, a phenyloxy group or a phenacyloxy group;
$R_2$ is a hydrogen atom, an alkaline metal, an optionally branched alkyl group having 1 to 6 carbon atoms, an acyl group having 1 to 6 carbon atoms or a phenylalkylene group;
Z is at least one group selected from the group consisting of a hydrogen atom, a halogen atom, a nitro group, a nitroso group and an amino group, Z may be substituted on any ring of the naphthalene ring; and
n is an integer of 1 or 2.

2. The naphthol derivative according to claim 1, wherein Y is —(COHN)$_n$—X and Y' is —(CONH)$_n$—X'.

3. The naphthol derivative according to claim 1, wherein Y is —(CONH)—X' and Y' is —COR.

4. The naphthol derivative according to claim 1, wherein Y is —COR and Y' is —(CONH)$_n$—X'.

* * * * *